United States Patent
He et al.

(10) Patent No.: US 12,430,900 B2
(45) Date of Patent: Sep. 30, 2025

(54) OBJECT RECOGNITION USING SPATIAL AND TIMING INFORMATION OF OBJECT IMAGES AT DIFERENT TIMES

(71) Applicant: Tencent Technology (Shenzhen) Company Limited, Guangdong (CN)

(72) Inventors: Nanjun He, Shenzhen (CN); Donghuan Lu, Shenzhen (CN); Yuexiang Li, Shenzhen (CN); Yi Lin, Shenzhen (CN); Kai Ma, Shenzhen (CN); Yefeng Zheng, Shenzhen (CN)

(73) Assignee: Tencent Technology (Shenzhen) Company Limited, Shenzhen (CN)

( * ) Notice: Subject to any disclaimer, the term of this patent is extended or adjusted under 35 U.S.C. 154(b) by 401 days.

(21) Appl. No.: 17/991,385

(22) Filed: Nov. 21, 2022

(65) Prior Publication Data

US 2023/0080098 A1    Mar. 16, 2023

Related U.S. Application Data

(63) Continuation of application No. PCT/CN2022/091089, filed on May 6, 2022.

(30) Foreign Application Priority Data

Jun. 3, 2021 (CN) .......................... 202110617124.4

(51) Int. Cl.
*G06V 10/80* (2022.01)
*G06V 10/26* (2022.01)
*G16H 30/40* (2018.01)

(52) U.S. Cl.
CPC ............ *G06V 10/806* (2022.01); *G06V 10/26* (2022.01); *G16H 30/40* (2018.01)

(58) Field of Classification Search
CPC ....... G06V 10/806; G06V 10/26; G16H 30/40
See application file for complete search history.

(56) References Cited

U.S. PATENT DOCUMENTS

| | | | |
|---|---|---|---|
| 7,088,850 B2 * | 8/2006 | Wei ....................... | G06T 7/0012 |
| | | | 382/128 |
| 11,403,761 B2 * | 8/2022 | Krebs ....................... | G06T 7/33 |
| (Continued) | | | |

FOREIGN PATENT DOCUMENTS

| | | |
|---|---|---|
| CN | 109117890 A | 1/2019 |
| CN | 109190540 A | 1/2019 |
| (Continued) | | |

OTHER PUBLICATIONS

Y. Li et al., "Computer-Aided Cervical Cancer Diagnosis Using Time-Lapsed Colposcopic Images," in IEEE Transactions on Medical Imaging, vol. 39, No. 11, pp. 3403-3415, Nov. 2020, doi: 10.1109/TMI.2020.2994778. (Year: 2020).*

(Continued)

*Primary Examiner* — Andrew M Moyer
*Assistant Examiner* — Conor A O'Malley
(74) *Attorney, Agent, or Firm* — ArentFox Schiff LLP

(57) ABSTRACT

An object recognition method includes extracting, by a first transformer network, spatial features of a plurality of medical images respectively, the plurality of medical images being images of a same object at different times, and fusing the extracted plurality of spatial features, to obtain a first fusion spatial feature of the object. The method further includes extracting, by a second transformer network, a spatial-temporal feature of the object based on the first fusion spatial feature. The spatial-temporal feature indicates a change in the spatial features of the plurality of medical images at the different times. The method further includes (Continued)

recognizing a state of the object based on the spatial-temporal feature, to obtain a recognition result of the object.

18 Claims, 12 Drawing Sheets

(56) References Cited

U.S. PATENT DOCUMENTS

| | | | | |
|---|---|---|---|---|
| 11,748,889 | B2* | 9/2023 | Guo | G06V 10/764 |
| | | | | 382/173 |
| 2010/0067768 | A1* | 3/2010 | Lonasec | G06T 7/344 |
| | | | | 382/128 |
| 2013/0294667 | A1* | 11/2013 | Zheng | G06T 7/30 |
| | | | | 382/131 |
| 2016/0093048 | A1* | 3/2016 | Cheng | G06V 10/82 |
| | | | | 382/131 |
| 2019/0057778 | A1* | 2/2019 | Porter | G16H 50/50 |
| 2019/0205606 | A1* | 7/2019 | Zhou | G06F 18/285 |
| 2019/0318497 | A1* | 10/2019 | Zhao | A61B 5/1128 |
| 2020/0311940 | A1* | 10/2020 | Krebs | G06T 7/246 |
| 2021/0233247 | A1* | 7/2021 | Cao | G16H 50/70 |
| 2021/0390338 | A1* | 12/2021 | Xu | G06F 18/214 |
| 2022/0208355 | A1* | 6/2022 | Li | G06T 7/174 |

FOREIGN PATENT DOCUMENTS

| | | | | |
|---|---|---|---|---|
| CN | 110363081 A | | 10/2019 | |
| CN | 110472532 A | | 11/2019 | |
| CN | 110490863 A | | 11/2019 | |
| CN | 110807495 A | * | 2/2020 | G06F 18/241 |
| CN | 111160162 A | | 5/2020 | |
| CN | 111755118 A | * | 10/2020 | G06F 18/24 |
| CN | 111832509 A | | 10/2020 | |
| CN | 112016461 A | | 12/2020 | |
| CN | 112102315 A | * | 12/2020 | G06K 9/6268 |
| CN | 112651267 A | | 4/2021 | |
| CN | 112836609 A | * | 5/2021 | |
| CN | 113610750 A | | 11/2021 | |
| CN | 113724186 A | * | 11/2021 | G06T 7/0012 |
| CN | 113762037 A | * | 12/2021 | |
| CN | 110633700 B | * | 3/2022 | G06K 9/00744 |
| CN | 114943670 A | * | 8/2022 | |
| WO | WO-2020177673 A1 | * | 9/2020 | G06F 40/279 |

OTHER PUBLICATIONS

Yu, S. et al. (2021). MIL-VT: Multiple Instance Learning Enhanced Vision Transformer for Fundus Image Classification. In: de Bruijne, M., et al. Medical Image Computing and Computer Assisted Intervention—MICCAI 2021. MICCAI 2021. Lecture Notes in Computer Science(), vol. 12908. Springer, Cham. (Year: 2021).*

Zhiqin Zhu, Yi Chai, Hongpeng Yin, Yanxia Li, Zhaodong Liu, A novel dictionary learning approach for multi-modality medical image fusion, Neurocomputing, vol. 214, 2016, pp. 471-482, ISSN 0925-2312 (Year: 2016).*

Zheng Y. Pericardium based model fusion of CT and non-contrasted C-arm CT for visual guidance in cardiac interventions. Med Image Comput Comput Assist Interv. 2014;17(Pt 2):700-7. doi: 10.1007/978-3-319-10470-6_87. PMID: 25485441. (Year: 2014).*

International Search Report and Written Opinion in PCT/CN2022/091089, mailed Jul. 6, 2022, 12 pages.

Chinese Search Report and Written Opinion in CN202110617124.4, mailed Oct. 27, 2021 with English Translation, 20 pages.

Chinese Office Action issued Dec. 21, 2023 in Application No. 202110617124.4 (23 pages).

Li, Y., Chen, J., Xue, P., Tang, C., Chang, J., Chu, C., Ma, K., Li, Q., Zheng, Y., Qiao, Y.: Computer-aided cervical cancer diagnosis using time-lapsed colposcopic images. IEEE Transactions on Medical Imaging 39(11), 3403-3415 (2020).

* cited by examiner

OBJECT RECOGNITION USING SPATIAL AND TIMING INFORMATION OF OBJECT IMAGES AT DIFERENT TIMES

RELATED APPLICATIONS

This application is a continuation of International Application No. PCT/CN2022/091089, filed on May 6, 2022, which claims priority to Chinese Patent Application No. 202110617124.4, entitled "OBJECT RECOGNITION METHOD AND APPARATUS, COMPUTER DEVICE, AND STORAGE MEDIUM", and filed on Jun. 3, 2021. The entire disclosures of the prior applications are hereby incorporated by reference.

FIELD OF THE TECHNOLOGY

Embodiments of this application relate to the field of computer technologies, including an object recognition method and apparatus, a computer device, and a storage medium.

BACKGROUND OF THE DISCLOSURE

As computer technologies advance, it has become a common approach to use image processing technology to assist object recognition. For example, in the medical field, a recognition result of a target object is obtained by performing recognition on an acquired medical image of the target object. Then, a state of the target object is determined according to the recognition result, or the medical image is segmented according to the recognition result.

SUMMARY

The embodiments of this disclosure provide an object recognition method and apparatus, a computer device, and a storage medium, which improves the recognition accuracy.

In an embodiment, an object recognition method includes extracting, by a first transformer network, spatial features of a plurality of medical images respectively, the plurality of medical images being images of a same object at different times, and fusing the extracted plurality of spatial features, to obtain a first fusion spatial feature of the object. The method further includes extracting, by a second transformer network, a spatial-temporal feature of the object based on the first fusion spatial feature. The spatial-temporal feature indicates a change in the spatial features of the plurality of medical images at the different times. The method further includes recognizing a state of the object based on the spatial-temporal feature, to obtain a recognition result of the object.

In an embodiment, an object recognition apparatus includes processing circuitry configured to extract, by a first transformer network, spatial features of a plurality of medical images respectively. The plurality of medical images are images of a same object at different times. The processing circuitry is further configured to fuse the extracted plurality of spatial features, to obtain a first fusion spatial feature of the object, and extract, by a second transformer network, a spatial-temporal feature of the object based on the first fusion spatial feature. The spatial-temporal feature indicates a change in the spatial features of the plurality of medical images at the different times. The processing circuitry is further configured to recognize a state of the object based on the spatial-temporal feature, to obtain a recognition result of the object.

In an embodiment, a non-transitory computer-readable storage medium stores computer-readable instructions thereon, which, when executed by processing circuitry, cause the processing circuitry to perform on object recognition method. The object recognition method includes extracting, by a first transformer network, spatial features of a plurality of medical images respectively, the plurality of medical images being images of a same object at different times, and fusing the extracted plurality of spatial features, to obtain a first fusion spatial feature of the object. The method further includes extracting, by a second transformer network, a spatial-temporal feature of the object based on the first fusion spatial feature. The spatial-temporal feature indicates a change in the spatial features of the plurality of medical images at the different times. The method further includes recognizing a state of the object based on the spatial-temporal feature, to obtain a recognition result of the object.

In accordance with the method, the apparatus, the computer device and the storage medium provided by the embodiments of this disclosure, first, the spatial features of the plurality of medical images of the target object are extracted respectively; after the spatial feature of each medical image is fully extracted, the plurality of spatial features are fused; and the spatial-temporal feature of the target object is extracted based on the obtained first fusion spatial feature. The spatial-temporal feature can characterize a change in the spatial information of the plurality of medical images at different times. In addition, the temporal relationship between the plurality of medical images is considered during extraction, so that the extracted spatial-temporal feature can more accurately represent the spatial information and the timing information of the plurality of medical images. Therefore, the recognition for the target object based on the spatial-temporal feature improves the accuracy of the recognition result.

BRIEF DESCRIPTION OF THE DRAWINGS

To describe the technical solutions in the embodiments of this disclosure, the following briefly introduces the accompanying drawings describing the embodiments. The accompanying drawings in the following description show only some embodiments of this disclosure, and a person of ordinary skill in the art may still derive other accompanying drawings from the accompanying drawings.

DESCRIPTION OF EMBODIMENTS

Figure 1:
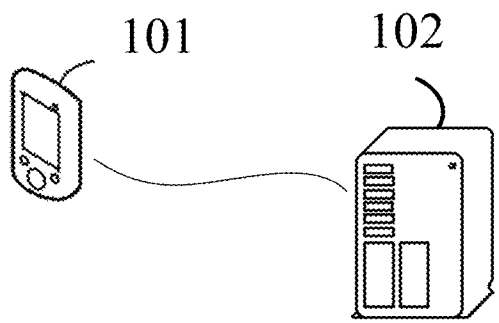
FIG. 1 is a schematic diagram of an implementation environment according to an embodiment of this disclosure.

To make objectives, technical solutions, and advantages of the embodiments of this disclosure clearer, the following further describes in detail implementations of this disclosure with reference to the accompanying drawings.

It may be understood that, the terms "first", "second", and the like used in this disclosure may be used for describing various concepts in this specification. However, the concepts are not limited by the terms unless otherwise specified. The terms are merely used for distinguishing one concept from another concept. For example, without departing from the scope of this disclosure, a first image feature may be referred to as a second image feature, and similarly, the second image feature may be referred to as the first image feature.

For the terms "at least one", "a plurality of", "each", "any one", etc. used herein, at least one includes one, two or more; a plurality of includes two or more; each refers to each one in a plurality of items; and any refers to any one in a plurality of items. For example, a plurality of medical images includes three medical images; each medical image refers to each one in the three medical images; and any one refers to any one in the three medical images, which may be the first one, the second one, or the third one.

The solution provided by the embodiments of this disclosure involves technologies such as computer vision, machine learning, etc. in artificial intelligence. By calling an image recognition model, the spatial features and the spatial-temporal feature of a target object are extracted, and the target object is recognized based on the spatial-temporal feature, to obtain a recognition result.

The object recognition method provided by the embodiments of this disclosure is performed by a computer device. In an embodiment, the computer device is a terminal or a server. The terminal may be a smartphone, a tablet computer, a notebook computer, a desktop computer, a smart speaker, a smartwatch, or the like, but is not limited thereto. The server may be an independent physical server, or may be a server cluster or a distributed system formed by a plurality of physical servers, or may be a cloud server that provides a basic cloud computing service such as a cloud service, a cloud database, cloud computing, a cloud function, cloud storage, a network service, cloud communication, a middleware service, a domain name service, a security service, a content delivery network (CDN), big data, and an artificial intelligence platform.

In a possible implementation, a computer program involved in the embodiments of this disclosure may be deployed and executed on one computer device, or executed on a plurality of computer devices located at a location, or executed on a plurality of computer devices that are distributed at a plurality of locations and interconnected through a communication network, the plurality of computer devices that are distributed at a plurality of locations and interconnected through a communication network forming a blockchain system.

In a possible implementation manner, the computer device used to recognize an object in the embodiments of this disclosure is a node in the blockchain system. This node extracts spatial features of a plurality of medical images of a target object, and extracts a spatial-temporal feature of the target object based on the spatial features of the plurality of medical images, and recognizes the target object based on the spatial-temporal feature, to obtain a recognition result. Then, this node or a node corresponding to another device in the blockchain may store the recognition result of the target object.

To facilitate understanding of the embodiments of this disclosure, key terms involved herein are explained.

Transformer: It is a kind of deep learning network structure, which includes a multi-head self-attention module, a multi-layer perceptron (MLP) and a regularization layer, and in which a residual structure is used. The multi-head self-attention module is obtained by cascading a plurality of self-attention modules. Outputted results of the plurality of self-attention modules are cascaded, thereby obtaining an outputted result of the multi-head self-attention module.

Convolutional Neural Network (CNN): It is a kind of deep learning network widely applied in image classification tasks, which includes at least a convolutional layer, a pooling layer or other processing layers.

Residual network (ResNet): It is a kind of CNN network structure. The ResNet is easy to be optimized, and alleviates the vanishing gradient problem caused by increasing the depth in deep neural network.

Computed tomography (CT) image: A CT image is an image that is obtained by using X-rays to scan a layer with a certain thickness in a human body or an object, receiving X-rays passing through the layer, and processing the received X-rays.

FIG. 1 is a schematic diagram of an implementation environment according to an embodiment of this disclosure. Referring to FIG. 1, the implementation environment includes at least a terminal 101 (one terminal 101 is shown in FIG. 1 as an example) and a server 102. The terminal 101 and the server 102 are connected through a wireless or wired network.

The terminal 101 is installed with a target application that is served by the server 102. Through this target application, the terminal 101 can realize functions such as image recognition, image transmission, etc. In an embodiment, the terminal 101 is a computer, a mobile phone, a tablet computer, etc. In an embodiment, the target application is a target application in an operating system of the terminal 101, or a target application provided by a third party. For example, the target application is a medical application, which has a function of recognizing medical images, and in addition, has other functions, such as generating medical records, displaying medical images, etc. In an embodiment, the server 102 is a back-end server of the target application or a cloud server that provides services such as cloud computing, cloud storage, etc.

Based on the implementation environment as shown in FIG. 1, an embodiment of this disclosure provides a scene of recognizing a state of a cervix. In this scene, the terminal acquires images of the same object' cervix every 30 seconds, to obtain five CT images, and transmits the five CT images to the server. The server extracts spatial features of the five CT images respectively, extracts a spatial-temporal feature of the object's cervix based on five spatial features, performs recognition based on the spatial-temporal feature, to obtain the object's cervix recognition result, and returns the cervix recognition result to the terminal. Subsequently, the cervix recognition result may be used as a basis for auxiliary judgment, and the state of the object's cervix may be determined in combination with other information of the object.

Based on the implementation environment as shown in FIG. 1, an embodiment of this disclosure further provides a scene of segmenting a CT image. In this scene, the terminal acquires images of the same object' cervix every 30 seconds, to obtain five CT images, and transmits the five CT images to the server. The server extracts spatial features of the five CT images respectively, extracts a spatial-temporal feature of the object's cervix based on five spatial features, performs recognition based on the spatial-temporal feature, to obtain the object's cervix recognition result, and returns the cervix recognition result to the terminal. The terminal determines a lesion region in each CT image according to the recognition result, and segments each CT image, to obtain the lesion region in each CT image, which facilitates further processing of the lesion region.

Figure 2:
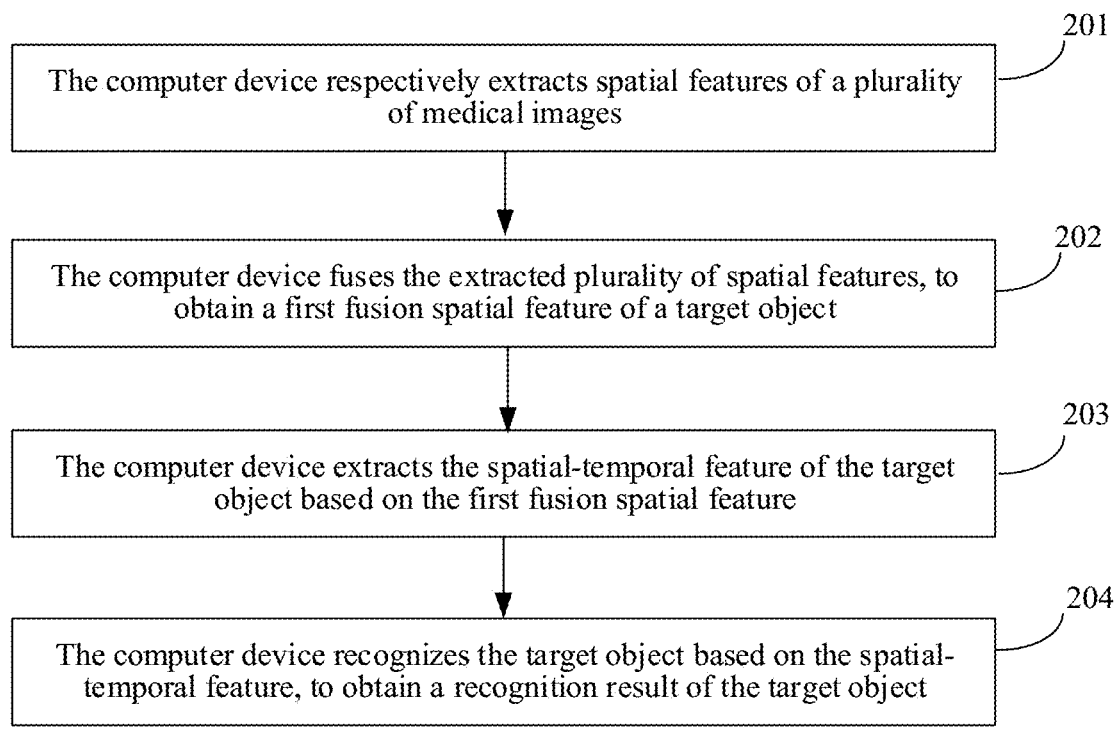
FIG. 2 is a flowchart of an object recognition method according to an embodiment of this disclosure.

FIG. 2 is a flowchart of an object recognition method according to an embodiment of this disclosure. An execution subject of this embodiment of this disclosure is a computer device. Referring to FIG. 2, the method includes the following steps:

201. The Computer Device Respectively Extracts Spatial Features of a Plurality of Medical Images.

For example, spatial features of a plurality of medical images are extracted respectively by a first transformer network. The plurality of medical images are images of a same object at different times.

The plurality of medical images are images of the same target object at different times. The target object is any object, such as a person or a certain part of a body. The spatial feature characterizes spatial information of the corresponding medical image. For example, the spatial information includes at least size information of the medical image, pixel values or position information of pixel points in the medical image. In addition, when the computer device extracts the spatial features of the plurality of medical images, the spatial feature extraction processes of the plurality of medical images are performed independently, without interfering with one another.

202. The Computer Device Fuses the Extracted Plurality of Spatial Features, to Obtain a First Fusion Spatial Feature of a Target Object.

For example, the extracted plurality of spatial features are fused, to obtain a first fusion spatial feature of the object.

In this embodiment of this disclosure, the computer device first extracts the spatial feature of each medical image respectively, and further extracts a spatial-temporal feature based on the extracted plurality of spatial features. Since a temporal relationship between the plurality of medical images needs to be considered during subsequent feature extraction, the extracted plurality of spatial features is first fused, to obtain the first fusion spatial feature.

203. The Computer Device Extracts the Spatial-Temporal Feature of the Target Object Based on the First Fusion Spatial Feature.

For example, a spatial-temporal feature of the object is extracted by a second transformer network, based on the first fusion spatial feature. The spatial-temporal feature indicates a change in the spatial features of the plurality of medical images at the different times.

In this embodiment of this disclosure, since the spatial-temporal feature is obtained by performing timing feature extraction based on the first fusion spatial feature, the extracted spatial-temporal feature includes the spatial information of each medical image and timing information of the plurality of medical images. The timing information of the plurality of medical images refers to a chronological order corresponding to the plurality of medical images and a change condition of the medical images at different times, that is, the spatial-temporal feature characterizes a change in the spatial information of the plurality of medical images at different times.

204. The Computer Device Recognizes the Target Object Based on the Spatial-Temporal Feature, to Obtain a Recognition Result of the Target Object.

For example, a state of the object is recognized based on the spatial-temporal feature, to obtain a recognition result of the object.

The recognition result is used for indicating a state of the target object. In an embodiment, the state of the target object includes a normal state and an abnormal state. Alternatively, the recognition result is used for indicating an abnormal region in each medical image.

In accordance with the method provided by this embodiment of this disclosure, first, the spatial features of the plurality of medical images of the target object are respectively extracted; after the spatial feature of each medical image is fully extracted, the plurality of spatial features is fused; and the spatial-temporal feature of the target object is extracted based on the first fusion spatial features obtained through the fusion. The spatial-temporal feature characterizes a change in the spatial information of the plurality of medical images at different moments. In addition, the temporal relationship between the plurality of medical images is considered during extraction, so that the extracted spatial-temporal feature can more accurately represent the spatial information and the timing information of the plurality of medical images. Therefore, the recognition for the target object based on the spatial-temporal feature improves the accuracy of the recognition result.

Figure 3:
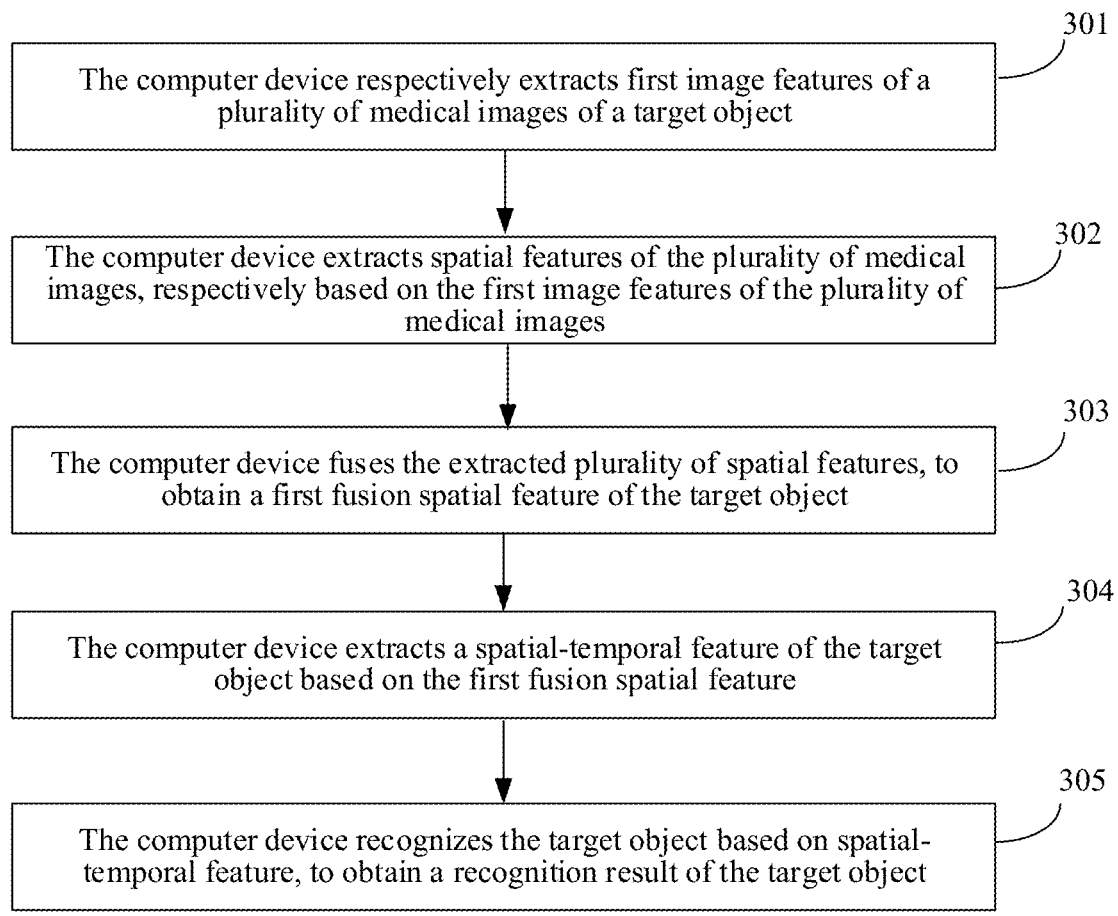
FIG. 3 is a flowchart of another object recognition method according to an embodiment of this disclosure.

FIG. 3 is a flowchart of another object recognition method according to an embodiment of this disclosure. An execution subject of this embodiment of this disclosure is a computer device. Referring to FIG. 3, the method includes the following steps:

301. The Computer Device Respectively Extracts First Image Features of a Plurality of Medical Images of a Target Object.

The target object is any object, and refers to a human body or a certain part of the human body. For example, the target object is any part such as lung, stomach, uterus, etc. The plurality of medical images are images of the same target object at different times, that is, the plurality of medical images are images obtained by acquiring the target object at different times. The medical images are CT images, or images captured by X-ray irradiation, or images acquired by other means. In an embodiment, the plurality of medical images is acquired by the computer device, or is transmitted to the computer device after being acquired by any other device, which is not limited herein.

An interval between acquisition times of any two adjacent medical images may be the same or different. For example, the interval is 30 seconds, 60 seconds, or other duration. For example, for four medical images, there is an interval of 30 seconds between the acquisition time of the first medical image and the acquisition time of the second medical image, 30 seconds between the acquisition time of the second medical image and the acquisition time of the third medical image, and 30 seconds between the acquisition time of the third medical image and the acquisition time of the fourth medical image.

The first image feature is used for describing the corresponding medical image. The first image feature is a vector, a matrix or of other form. In a possible implementation, the computer device encodes the plurality of medical images respectively, to obtain the first image feature of each medical image.

302. The Computer Device Extracts Spatial Features of the Plurality of Medical Images, Respectively Based on the First Image Features of the Plurality of Medical Images.

The spatial feature characterizes spatial information of the corresponding medical image. For example, the spatial information includes at least size information of the medical image, pixel values or position information of pixel points in the medical image. The spatial feature is a vector, a matrix or of other form.

When the computer device extracts the spatial features of the plurality of medical images, the spatial feature extraction processes of the plurality of medical images are performed independently, without interfering with one other. Taking the spatial feature of any medical image as an example, the process of extracting the spatial feature is described below.

In a possible implementation, the medical image is segmented into a plurality of image regions, that is, the medical image includes a plurality of image regions. Correspondingly, the computer device segments the first image feature of the medical image into a plurality of region features, each of which corresponding to one image region in the medical image, and in addition, obtains first attention parameters corresponding to the plurality of region features respectively, and performs weighted fusion on the plurality of region features based on the plurality of first attention parameters, to obtain a second image feature corresponding to the medical image; and extracts the spatial feature of the medical image based on the second image feature.

The first attention parameter of a region feature characterizes an importance degree of the corresponding region feature in the first image feature. The second image feature is used for describing the corresponding medical image. A difference between the first image feature and the second image feature lies in that: on the basis of the first image feature, the second image feature is obtained by adjusting the first image feature according to the importance degrees of different region features. The second image feature can more accurately characterize a more important image region in the medical image, when compared with the first image feature.

For determining the first attention parameter, in a possible implementation, the computer device maps each region feature to at least two feature spaces, to obtain at least two mapping features corresponding to each region feature, the at least two feature spaces characterizing a similarity of different pixels in the corresponding image region in a corresponding dimension; and obtains the first attention parameter corresponding to each region feature, based on the at least two mapping features corresponding to each region feature.

In a possible implementation, the computer device extracts the spatial feature of the medical image based on the second image feature, including: the computer device directly performing spatial feature extraction on the second image feature, to obtain the spatial feature of the medical image.

In another possible implementation, in order to avoid losing information during the process in which the first image feature is processed to obtain the second image feature, leading to inaccurate extracted spatial feature, the computer device fuses the second image feature and the first image feature, to obtain a third image feature corresponding to the medical image; and extracts the spatial feature of the medical image based on the third image feature. The third image feature includes the first image feature and the second image feature, so it includes complete information of the medical image, and at the same time, can highlight information about the more important image region in the medical image.

In addition, in a possible implementation, in order to reduce the calculation amount during the processing process and thereby enhancing the processing speed, the computer device first performs normalization processing on the first image feature, to obtain a processed first image feature; and then performs the step of determining the first attention parameters for the first image feature that has undergone the normalization processing. Similarly, the computer device performs normalization processing on the third image feature, to obtain a processed third image feature; and then performs the step of performing the spatial feature extraction for the third image feature that has undergone the normalization processing. The normalization processing can limit values included in the image feature to a range of 0 to 1, which avoids large differences between the values included in the image feature, thereby avoiding a complicated processing process.

The process of extracting the spatial feature is described with one medical image as an example. Any of the foregoing implementations may be used to extract the corresponding spatial feature for each medical image in this disclosure.

This embodiment of this disclosure has no limitation on the order of extracting the spatial features of the plurality of medical images. In an embodiment, the spatial features of the plurality of medical images are extracted simultaneously; or, the spatial feature of each medical image is extracted sequentially according to the acquisition time corresponding to the medical image.

303. The Computer Device Fuses the Extracted Plurality of Spatial Features, to Obtain a First Fusion Spatial Feature of the Target Object.

In this embodiment of this disclosure, the computer device first extracts the spatial feature of each medical image, and then performs timing feature extraction based on the extracted plurality of spatial features. When performing the timing feature extraction, a temporal relationship is considered between the plurality of medical images, rather than performing the timing feature extraction for each spatial feature. Therefore, the plurality of spatial features needs to be fused, to obtain the first fusion spatial feature.

The fusion of the plurality of spatial features may be stitching the plurality of spatial features, so that the obtained first fusion spatial feature includes the spatial features of the plurality of medical images.

304. The Computer Device Extracts a Spatial-Temporal Feature of the Target Object Based on the First Fusion Spatial Feature.

Since the spatial-temporal feature is obtained by performing the timing feature extraction based on the first fusion spatial feature, the extracted spatial-temporal feature includes the spatial information of each medical image and timing information of the plurality of medical images. The timing information of the plurality of medical images refers to a chronological order corresponding to the plurality of medical images and a change condition of the medical images at different times, that is, the spatial-temporal feature characterizes a change in the spatial information of the plurality of medical images at different times. That is, the spatial-temporal feature characterizes a change condition of the plurality of medical images.

In a possible implementation, the computer device segments the first fusion spatial feature into a plurality of spatial sub-features according to the medical images, each spatial sub-feature corresponding to one medical image, to obtain second attention parameters corresponding to the plurality of spatial sub-features; fuses the plurality of spatial sub-features based on the plurality of second attention parameters, to obtain a second fusion spatial feature corresponding to the plurality of medical images; and extracts the spatial-temporal feature based on the second fusion spatial feature. The second attention parameter characterizes an importance degree of the corresponding spatial sub-feature in the first fusion spatial feature.

For determining the second attention parameter, in a possible implementation, the computer device maps each spatial sub-feature to at least two feature spaces, to obtain at least two mapping features corresponding to each spatial sub-feature, the at least two feature spaces characterizing a similarity of different pixels in the corresponding medical image in a corresponding dimension; and obtains the second attention parameter corresponding to each spatial sub-feature based on the at least two mapping features corresponding to each spatial sub-feature.

In a possible implementation, the computer device extracts the spatial feature of the medical images based on the second fusion spatial feature, including: the computer device directly performing timing feature extraction on the second fusion space, to obtain the spatial-temporal feature.

In another possible implementation, in order to avoid losing information in the first fusion spatial feature during the process in which the first fusion spatial feature is processed to obtain the second fusion spatial feature, leading to inaccurate extracted spatial feature, the computer device fuses the second fusion spatial feature and the first fusion spatial feature, to obtain a third fusion spatial feature of the target object; and extracts the spatial-temporal feature based on the third fusion spatial feature. The third fusion spatial feature includes the first fusion spatial feature and the second fusion spatial feature, so it includes the spatial information of all of the medical images, and at the same time, can highlight information about the more important medical image in the plurality of medical images.

In addition, in a possible implementation, in order to reduce the calculation amount during the processing process and thereby enhancing the processing speed, the computer device first performs normalization processing on the first fusion spatial feature, to obtain a processed first fusion spatial feature, and then performs the step of determining the second attention parameters for the first fusion spatial feature that has undergone the normalization processing. Similarly, the computer device performs normalization processing on the third fusion spatial feature, to obtain a processed third fusion spatial feature, and then performs the step of extracting the spatial-temporal feature for the third fusion spatial feature that has undergone the normalization processing.

305. The Computer Device Recognizes the Target Object Based on the Spatial-Temporal Feature, to Obtain a Recognition Result of the Target Object.

The recognition result is used for indicating a state of the target object, or used for indicating an abnormal region in each medical image.

In a possible implementation, the state of the target object includes a normal state and an abnormal state. The normal state indicates that the target object has no change, and the abnormal state indicates that the target object has changed relative to its the normal state. For example, in a scene of performing disease recognition on the target object, the normal state indicates that the target object has no lesions, and the abnormal state indicates that the target object has lesions. In an embodiment, the recognition result includes a first category and a second category. The first category indicates that the target object is in the normal state, and the second category indicates that the target object is in the abnormal state. For example, the first category is negative, and the second category is positive.

In a possible implementation, the abnormal region in the medical image refers to a region where a lesion is present in the medical image, for example, the abnormal region is a lesion region. Correspondingly, the normal region in the medical image refers to a region where no lesion is present in the medical image. Based on the recognition result, the computer device segments each medical image respectively, to obtain the abnormal region in each medical image. That is, the abnormal region in each medical image is segmented, which facilitates further processing of the segmented abnormal region. For example, the computer device segments the CT image of the cervix, to obtain a lesion region in the CT image, and further recognizes the lesion region, to determine a size, shape, etc. of the lesion region, thereby obtaining more accurate information about the lesion region.

In the medical field, the recognition result obtained in this embodiment of this disclosure is only a basis for assisting a doctor to recognize a disease. For example, in a scene of recognizing cancer, the doctor needs to recognize whether the target object has cancer, in combination with the recognition result of the target object, other information related to the cancer, and a physical condition of the target object.

In accordance with the method provided by this embodiment of this disclosure, first, the spatial features of the plurality of medical images of the target object are extracted respectively; after the spatial feature of each medical image is fully extracted, the plurality of spatial features is fused; and the spatial-temporal feature of the target object is extracted based on the obtained first fusion spatial feature. The spatial-temporal feature can characterize the change in the spatial information of the plurality of medical images at different moments. In addition, the temporal relationship between the plurality of medical images is considered during extraction, so that the extracted spatial-temporal feature can more accurately represent the spatial information and the timing information of the plurality of medical images. Therefore, the recognition for the target object based on the spatial-temporal feature improves the accuracy of the recognition result.

In addition, in this embodiment of this disclosure, when extracting the spatial feature, the first image feature and the second image feature are fused, and the spatial feature extraction is performed on the third image feature obtained through fusion, so that more information can be used when extracting the spatial feature. This further improves the accuracy of the spatial feature, and avoids losing information in the first image feature during the process of obtaining the second image feature, resulting in inaccurate spatial feature extraction. Similarly, when extracting the spatial-temporal feature, the first fusion spatial feature and the second fusion spatial feature are fused, and the timing feature extraction is performed on the third fusion spatial feature obtained through fusion, so that more information can be used when extracting the spatial-temporal feature. This further improves the accuracy of the spatial-temporal feature, and avoids losing information in the first fusion spatial feature during the process of obtaining the second fusion spatial feature, resulting in inaccurate spatial feature extraction.

In addition, in this embodiment of this disclosure, the first attention parameter corresponding to each region feature in the first image feature is used to obtain the second image feature corresponding to the first image feature, so that the second image feature can highlight the region feature of the more important image region. Similarly, the second attention parameter corresponding to each spatial sub-feature in the first fusion spatial feature is used to obtain the second fusion spatial feature corresponding to the first fusion spatial feature, so that the second fusion spatial feature can highlight the spatial feature of the more important medical image.

As an example, this embodiment shown in FIG. 3 describes that the computer device directly processes the plurality of medical images, so as to realize the object recognition. In another embodiment, the computer device calls an image recognition model to process the plurality of medical images, so as to realize the object recognition. First, a structure of the image recognition model is introduced below.

Figure 4:
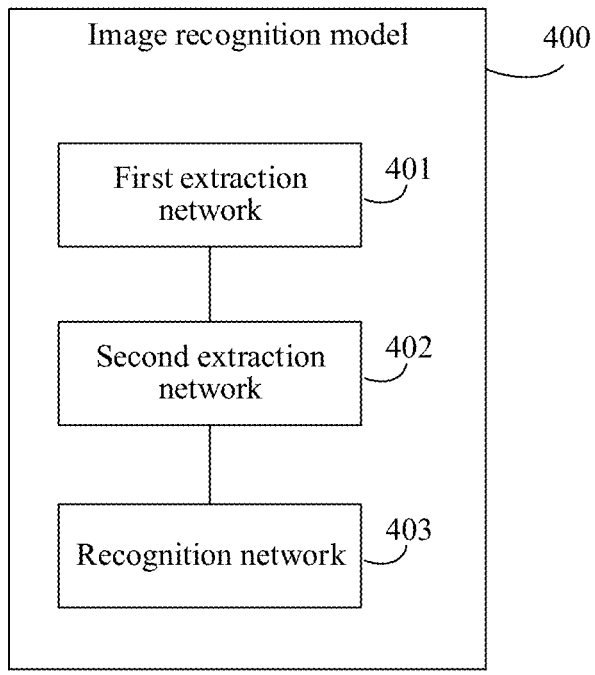
FIG. 4 is a schematic structural diagram of an image recognition model according to an embodiment of this disclosure.

Referring to FIG. 4, the image recognition model 400 includes a first extraction network 401, a second extraction network 402, and a recognition network 403. The first extraction network 401 is connected with the second extraction network 402, and the second extraction network 402 is also connected with the recognition network 403. The first extraction network 401 is used to extract a spatial feature of a medical image, the second extraction network 402 is used to extract a spatial-temporal feature of a target object, and the recognition network 403 is used to recognize the target object.

In a possible implementation, the image recognition model 400 is transformer in transformer (TiT). That is, the image recognition model 400 is cascaded transformers, and the TiT is obtained by cascading at least two transformers. The first extraction network and the second extraction network each is one transformer.

Figure 5:
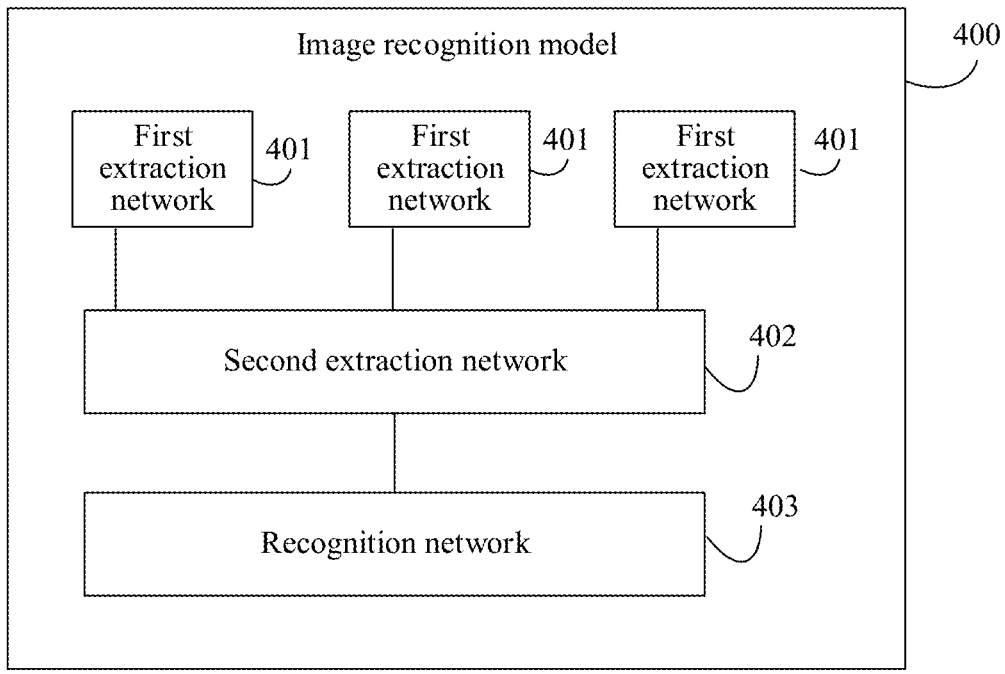
FIG. 5 is a schematic structural diagram of another image recognition model according to an embodiment of this disclosure.

In an embodiment, a different first extraction network 401 is used to extract the spatial feature for each medical image. In this case, referring to FIG. 5, the image recognition model 400 includes a plurality of first extraction networks 401 (e.g., 3 as shown in FIG. 5). Each first extraction network 401 is used to extract the spatial feature based on one medical image. The plurality of first extraction networks 401 are connected to the second extraction network 402 respectively.

Figure 6:
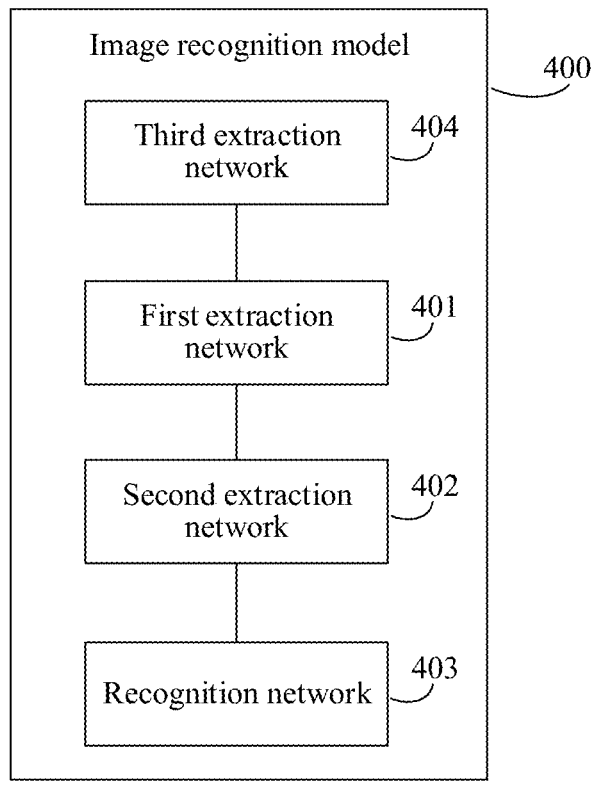
FIG. 6 is a schematic structural diagram of another image recognition model according to an embodiment of this disclosure.

Referring to FIG. 6, the image recognition model 4001 may further include a third extraction network 404. The third extraction network 404 is connected to the first extraction network 401, and is used to extract an image feature of a medical image, namely converting the medical image into a form which can be processed by the computer device. In the case that the image recognition model 400 includes a plurality of first extraction networks 401, the third extraction network 404 is connected to each first extraction network 401 respectively.

Figure 7:
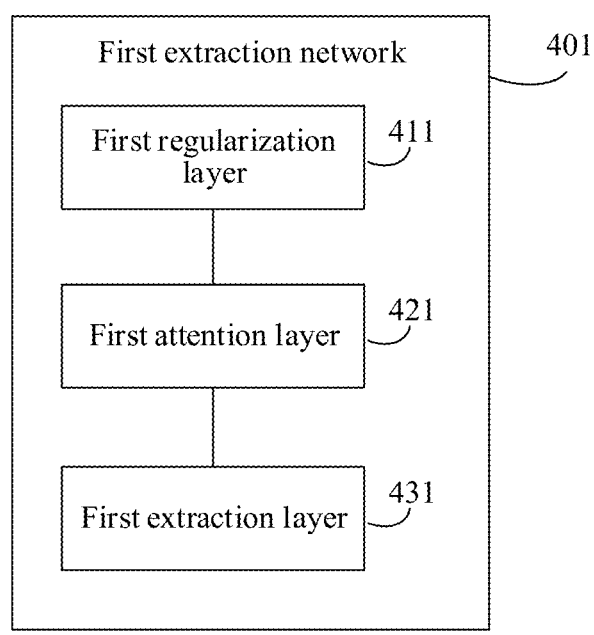
FIG. 7 is a schematic structural diagram of a first extraction network according to an embodiment of this disclosure.

In a possible implementation, the first extraction network 401 has a similar network structure as the second extraction network 402. Taking the network structure of the first extraction network 401 as an example, referring to FIG. 7, the first extraction network 401 includes a first regularization layer 411, a first attention layer 421, and a first extraction layer 431. The first regularization layer 411 is connected with the first attention layer 421, and the first attention layer 421 is also connected with the first extraction layer 431.

Figure 8:
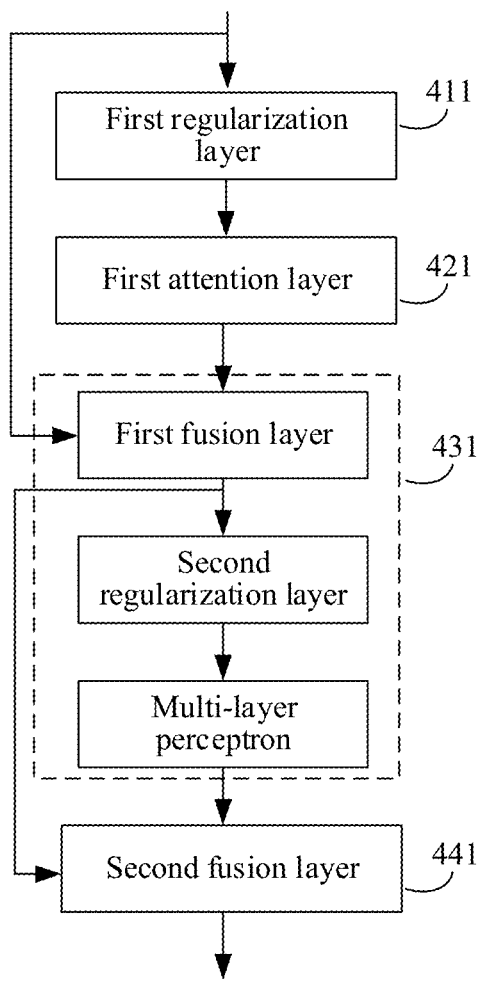
FIG. 8 is a schematic structural diagram of another first extraction network according to an embodiment of this disclosure.

Referring to FIG. 8, the first extraction layer 431 may include a first fusion layer, a second regularization layer, and a multi-layer perceptron. The first extraction network 401 further includes a second fusion layer 441. The first fusion layer is connected with the last layer of the previous network, the first attention layer 421 and the second regularization layer. The second regularization layer is also connected with the multi-layer perceptron. The multi-layer perceptron is also connected with the second fusion layer 441. The second fusion layer is also connected with the first fusion layer.

Figure 9:
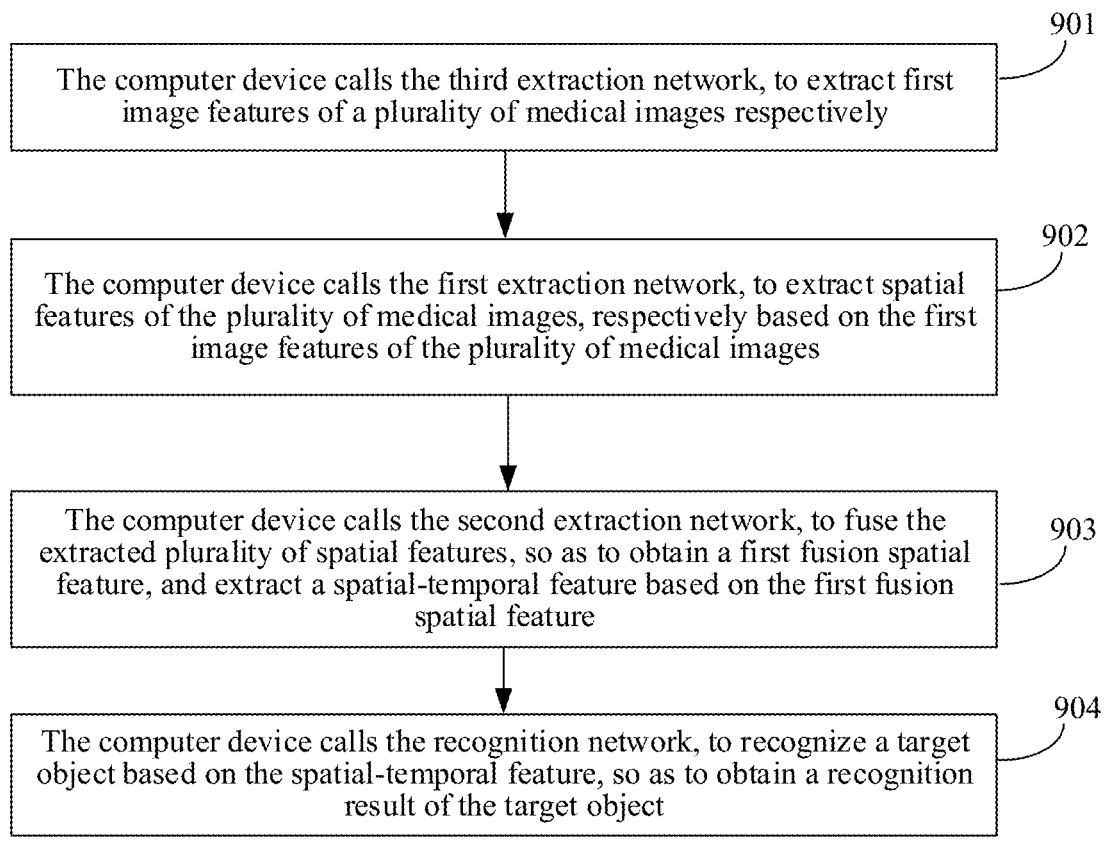
FIG. 9 is a flowchart of another object recognition method according to an embodiment of this disclosure.

The following is a detailed description of a process in which the above image recognition model is called to perform the object recognition. FIG. 9 is a flowchart of another object recognition method according to an embodiment of this disclosure. An execution subject of this embodiment of this disclosure is a computer device. Referring to FIG. 9, the method includes the following steps:

901. The Computer Device Calls the Third Extraction Network, to Extract First Image Features of a Plurality of Medical Images Respectively.

The third extraction network is used to encode the medical images, so as to obtain the first image features of the medical images.

In an embodiment, the image recognition model includes one third extraction network, which extracts the first image features of the plurality of medical images in sequence; or, the image recognition model includes a plurality of third extraction networks, each of which extracts the first image feature of one medical image.

For example, the third extraction network uses the following formula to extract the first image features of the plurality of medical images:

$$M=\text{Encoder}(x)$$

M represents an extracted first image feature, x represents an inputted medical image, and Encoder(−) represents using a CNN to perform the extraction.

A resolution (length×width) of any medical image is H×W, a quantity of channels of any medical image is C, a quantity of the medical images is T, and both C and T are positive integers.

902. The Computer Device Calls the First Extraction Network, to Extract Spatial Features of the Plurality of Medical Images, Respectively Based on the First Image Features of the Plurality of Medical Images.

In this embodiment of this disclosure, in the case that the image recognition model includes only one first extraction network, the computer device calls this first extraction network, to extract the spatial features sequentially based on the first image features of the plurality of medical images, so as to obtain the plurality of spatial features. In the case that the image recognition model includes a plurality of first extraction networks, the computer device calls one first extraction network, to extract the spatial feature based on the first image feature of one medical image, so as to obtain the spatial feature of this medical image.

The process in which any first extraction network extracts the spatial feature of the medical image is the same. The process of extracting the spatial feature is described below with any first extraction network as an example.

In a possible implementation, the first extraction network includes the first attention layer and the first extraction layer. For each medical image, the computer device calls the first attention layer, to segment the first image feature of the medical image into a plurality of region features, and obtain first attention parameters corresponding to the plurality of region features respectively, and fuse the plurality of region features according to the plurality of first attention parameters, so as to obtain a second image feature corresponding to the medical image; and calls the first extraction layer, to extract the spatial feature of the medical image based on the second image feature. The first attention parameter characterizes an importance degree of the corresponding region feature in the first image feature. Each region feature corresponds to one image region in the medical image. The medical image includes a plurality of image regions.

For determining the first attention parameter, in a possible implementation, the computer device calls the first attention layer, to map each region feature to at least two feature spaces respectively, so as to obtain at least two mapping features corresponding to each region feature; and obtain the first attention parameter corresponding to each region feature based on the at least two mapping features corresponding to each region feature.

For example, the computer device calls the first attention layer, to map each region feature to three feature spaces, which correspond to a query dimension, a key dimension, and a value feature dimension respectively. The following formulas are used to determine the first attention parameter corresponding to each region feature:

$$[q, k, v] = yU_{qkv} \quad A = \text{softmax}\left(\frac{qk}{\sqrt{D_h}}\right)$$

q represents a mapping feature of the query dimension, k represents a mapping feature of the key dimension, v represents a mapping feature of the value feature dimension, y represents any region feature, $U_{qkv}$ represents a model parameter obtained through training, A represents the first attention parameter corresponding to any region feature, softmax(•) represents normalization processing, and $D_h$ represents the number of dimensions of hidden layers in the first attention layer.

Correspondingly, the following formula is used to determine the second image feature corresponding to the medical image:

$$SA(y)=Av$$

$$MSA(y)=[sA_1(y);SA_2(y); \ldots ;SA_k(y)]U_{mas}$$

SA(y) represents a region feature after performing weighting on any region feature, MSA(y) represents the second image feature, k represents that the medical image has been segmented into k image regions, and $U_{mas}$ represents a model parameter obtained through training.

In a possible implementation, the first extraction network includes the residual network structure, that is, the first extraction network further includes the first fusion layer. The computer device calls the first fusion layer, to fuse the second image feature and the first image feature, so as to obtain a third image feature corresponding to the medical image; and calls the first extraction layer, to extract the spatial feature of the medical image based on the third image feature.

In addition, in a possible implementation, in order to reduce the calculation amount during the processing process and thereby enhancing the processing speed, the first extraction network further includes the first regularization layer and the second regularization layer. The computer device calls the first regularization layer, to perform the normalization processing on the first image feature, so as to obtain a processed first image feature. Similarly, the computer device calls the second regularization layer, to perform the normalization processing on the third image feature, so as to obtain a processed third image feature.

In an embodiment, the first extraction layer includes the multi-layer perceptron. The computer device calls the multi-layer perceptron, to extract the spatial feature based on the third image feature.

In a possible implementation, in order to avoid losing information in the third image feature during the process in which the third image feature is processed to obtain the spatial feature, leading to inaccurate extracted spatial-temporal feature, the computer device fuses the third image feature and the spatial feature, to obtain a fused spatial feature, and subsequently processes the fused spatial feature.

903. The Computer Device Calls the Second Extraction Network, to Fuse the Extracted Plurality of Spatial Features, so as to Obtain a First Fusion Spatial Feature, and Extract a Spatial-Temporal Feature Based on the First Fusion Spatial Feature.

In a possible implementation, the second extraction network includes a third fusion layer. The computer device calls the third fusion layer, to fuse the plurality of spatial features, so as to obtain the first fusion spatial feature. For example, the following formula is used in the third fusion layer, to obtain the first fusion spatial feature:

$$z=[ST(\hat{m}_1)_0;ST(\hat{m}_2)_0; \ldots ;ST(\hat{m}_T)_0]$$

z represents a first fusion spatial feature, $ST(\hat{m}_1)_0$ represents a spatial feature of an inputted medical image, and T represents a total of T medical images. Compared with the output MSA(y) obtained in step 902, $ST(\hat{m}_1)$ is obtained by splicing one row or one column of model parameters obtained through training into MSA(y).

In a possible implementation, the second extraction network has a similar network structure as the first extraction network. The second extraction network includes the second attention layer and the second extraction layer. The computer device calls the second attention layer, to segment the first fusion spatial feature into a plurality of spatial sub-features, and obtain second attention parameters corresponding to the plurality of spatial sub-features, and fuse the plurality of spatial sub-features based on the plurality of second attention parameters, so as to obtain a second fusion spatial feature corresponding to the plurality of medical images; and calls the second extraction layer, to extract the spatial-temporal feature based on the second fusion spatial feature.

For determining the second attention parameter, in a possible implementation, the computer device calls the second attention layer, to map each spatial sub-feature to at least two feature spaces respectively, so as to obtain at least two mapping features corresponding to each spatial sub-feature; and obtain the second attention parameter corresponding to each spatial sub-feature based on the at least two mapping features corresponding to each spatial sub-feature.

In a possible implementation, the second extraction network includes the residual network structure, that is, the second extraction network further includes a fourth fusion layer. The computer device calls the fourth fusion layer, to fuse the second fusion spatial feature and the first fusion spatial feature by, so as to obtain a third fusion spatial feature of the target object; and calls the second extraction layer, to extract the spatial-temporal feature based on the third fusion spatial feature.

In addition, in a possible implementation, in order to reduce the calculation amount during the processing process and thereby enhancing the processing speed, the second extraction network further includes a third regularization layer and a fourth regularization layer. The computer device calls the third regularization layer, to perform the normalization processing on the first fusion spatial feature, so as to obtain a processed first fusion spatial feature. Similarly, the computer device calls the fourth regularization layer, to perform the normalization processing on the third fusion spatial feature, to obtain a processed third fusion spatial feature.

In an embodiment, the second extraction layer includes the multi-layer perceptron. The computer device calls the multi-layer perceptron, to perform the timing feature extraction on the third fusion spatial feature, so as to obtain the spatial-temporal feature.

For example, the following formula is used in the second extraction network to extract the spatial-temporal feature:

$$f = TT(\hat{z})$$

f represents a spatial-temporal feature, $TT(\cdot)$ represents performing the timing feature extraction, and $TT(\cdot)$ represents a first fusion spatial feature. Compared with z obtained through fusion, $\hat{z}$ is obtained by splicing one row or one column of model parameters obtained through training into z.

This embodiment of this disclosure only takes one second extraction layer as an example for description. In another embodiment, the image recognition model includes a plurality of second extraction layers. A spatial-temporal feature outputted by the current second extraction layer is input to the subsequent second extraction layer, until a spatial-temporal feature outputted by the last second extraction layer is obtained. The spatial-temporal feature outputted by the last second extraction layer is determined as the spatial-temporal feature of the target object.

904. The Computer Device Calls the Recognition Network, to Recognize a Target Object Based on the Spatial-Temporal Feature, so as to Obtain a Recognition Result of the Target Object.

The recognition network is used to recognize the target object, to obtain the recognition result of the target object.

In a possible implementation, the recognition network includes a MLP and an activation function Softmax. The computer device calls the MLP and the activation function Softmax, to recognize the target object, so as to obtain the recognition result.

In a possible implementation, an output of the recognition network is 0 or 1. In a case that the output is 1, the target object is in the normal state; and in a case that the output is 0, the target object is in the abnormal state. Alternatively, the output of the recognition network is a probability. In a case that the outputted probability is greater than a reference probability, it indicates that the target object is in the normal state; and in a case that the outputted probability is not greater than the reference probability, it indicates that the target object is in the abnormal state.

Figure 10:
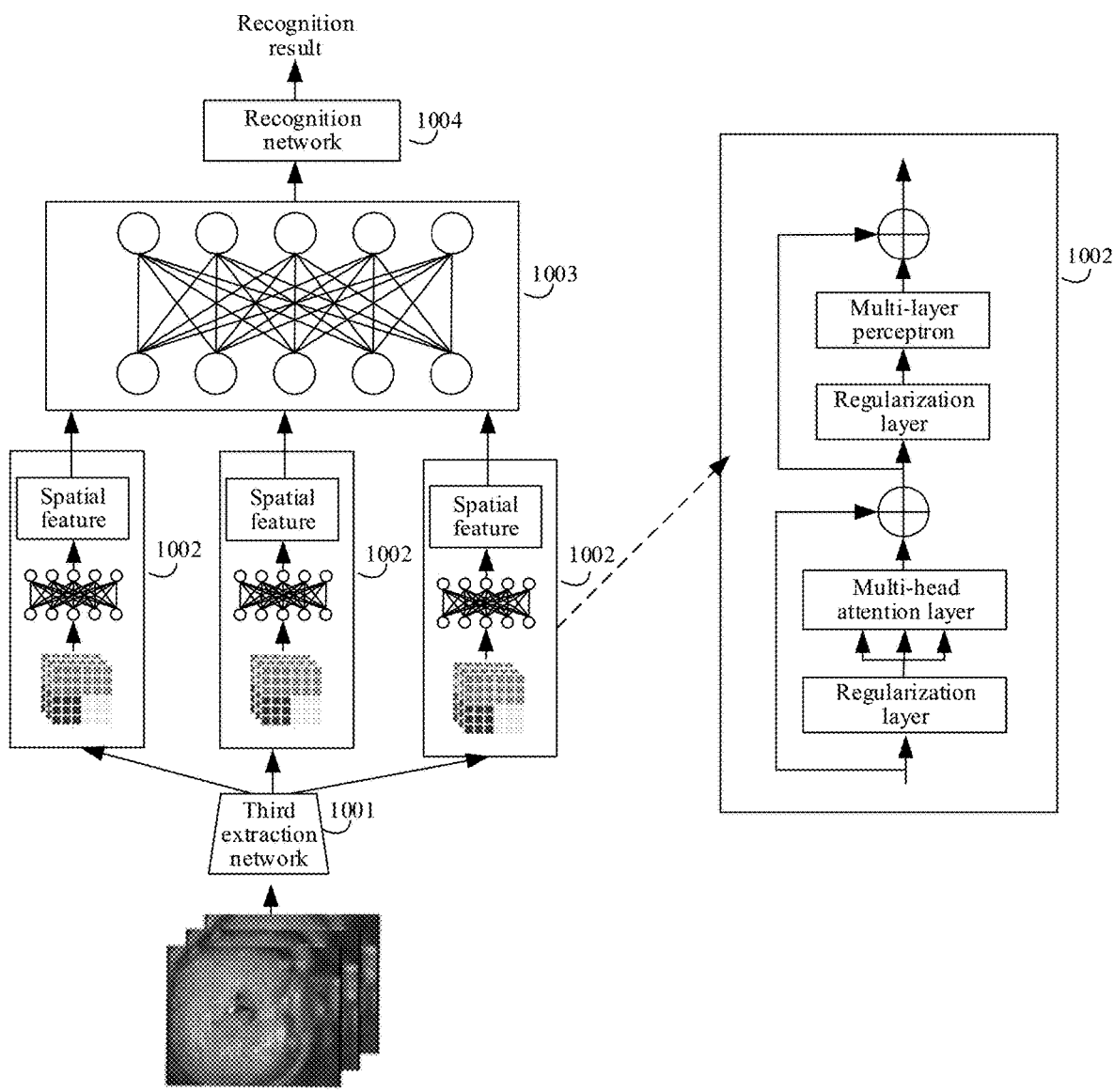
FIG. 10 is a schematic structural diagram of another image recognition network according to an embodiment of this disclosure.

For example, referring to FIG. 10, as an example, a target object has three medical images. First, the third extraction network 1001 extracts image features corresponding to the three medical images. The obtained three first image features are respectively input to the corresponding first extraction networks 1002, to allow the first extraction networks 1002 to output spatial features. The three spatial features are input to the second extraction network 1003, to allow the second extraction network 1003 to output a spatial-temporal feature of the target object. Then, the spatial-temporal feature is input into the recognition network 1004, to obtain a recognition result of the target object. In any first extraction network 1002, the normalization processing is performed on the first image feature by the regularization layer, and the processed first image feature is mapped to three feature spaces respectively. The three mapping features obtained through the mapping are processed by the multi-head attention layer, to output the second image feature. The first image feature and the second image feature are fused, to obtain the third image feature. Then, the normalization processing is performed on the third image feature by the regularization layer, to obtain the processed third image feature. The processed third image feature is input to the multi-layer perceptron, and after being processed by the multi-layer perceptron, the corresponding spatial feature is obtained. Then, the spatial feature is fused with the third image feature by the fusion layer, to obtain the fused spatial feature.

In another possible implementation, the computer device calls the recognition network, to recognize each medical image of the target object respectively; labels the abnormal region in the medical image after recognizing the abnormal region in each medical image; and outputs the labeled medical image. For example, the abnormal region in the medical image is circled with a color solid line, or is filled with a color that is not present in the medical image, or is labeled in other manners, which is not limited herein.

Figure 11:
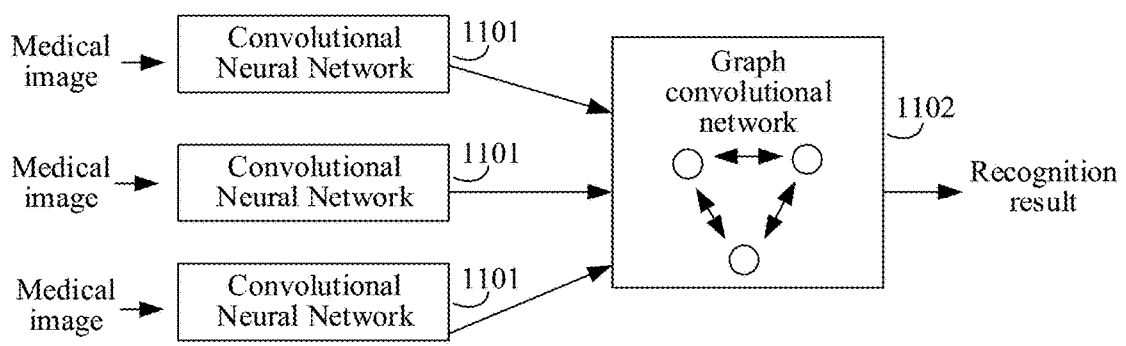
FIG. 11 is a schematic diagram of a heat map according to an embodiment of this disclosure.

In addition, a structure of the image recognition model is provided in the related art. Referring to FIG. 11, as an example, a target object has three medical images. The feature extraction is performed on these three medical images respectively by corresponding convolutional neural networks 1101. The extracted three features are input into the graph convolutional network 1102. The graph convolutional network 1102 fuses the three features, and performs recognition on the fused feature, to obtain a recognition result. One circle in the graph convolutional network 1102 represents one feature obtained through extraction.

This disclosure is compared with related art:

In the related art, a corresponding convolutional neural network needs to be trained separately for each medical image, resulting in a large amount of training, difficulty in model training, and low recognition efficiency. Moreover, since features are extracted respectively for different medical images, without full consideration of the relationship between different medical images. Therefore, the spatial information and the timing information of the plurality of medical images are not fully utilized, resulting in low recognition accuracy.

In addition, the image recognition models in the related art include an early fusion model, a voting model, a MLP, a long short-term memory (LSTM) Network, and a graph convolutional network (GCN). The recognition result of the image recognition model TiT in this disclosure is compared with the recognition results of the image recognition models in related art, and precision, recall, accuracy, and the number of parameters in a model are used to evaluate the recognition results. It can be seen that the image recognition model in this disclosure has a higher recognition accuracy and a simpler training process. The comparison result is shown in Table 1 below. It can be seen from Table 1 that the precision, recall and accuracy of the recognition result obtained using the image recognition model in this disclosure are the largest; and in addition, the number of parameters that the image recognition model in this disclosure needs to learn is less, when compared with the GCN.

TABLE 1

| Model | Precision | Recall | Accuracy | Quantity of parameters |
|---|---|---|---|---|
| Early fusion | 67.96 | 73.71 | 71.01 | — |
| Voting | 80.34 | 80.27 | 80.39 | — |
| MLP | 80.77 | 80.62 | 80.78 | — |
| LSTM | 80.59 | 80.40 | 80.59 | — |
| GCN | 81.97 | 81.78 | 81.95 | 233 |
| TiT | 85.70 | 83.08 | 82.80 | 57 |

Figure 12:
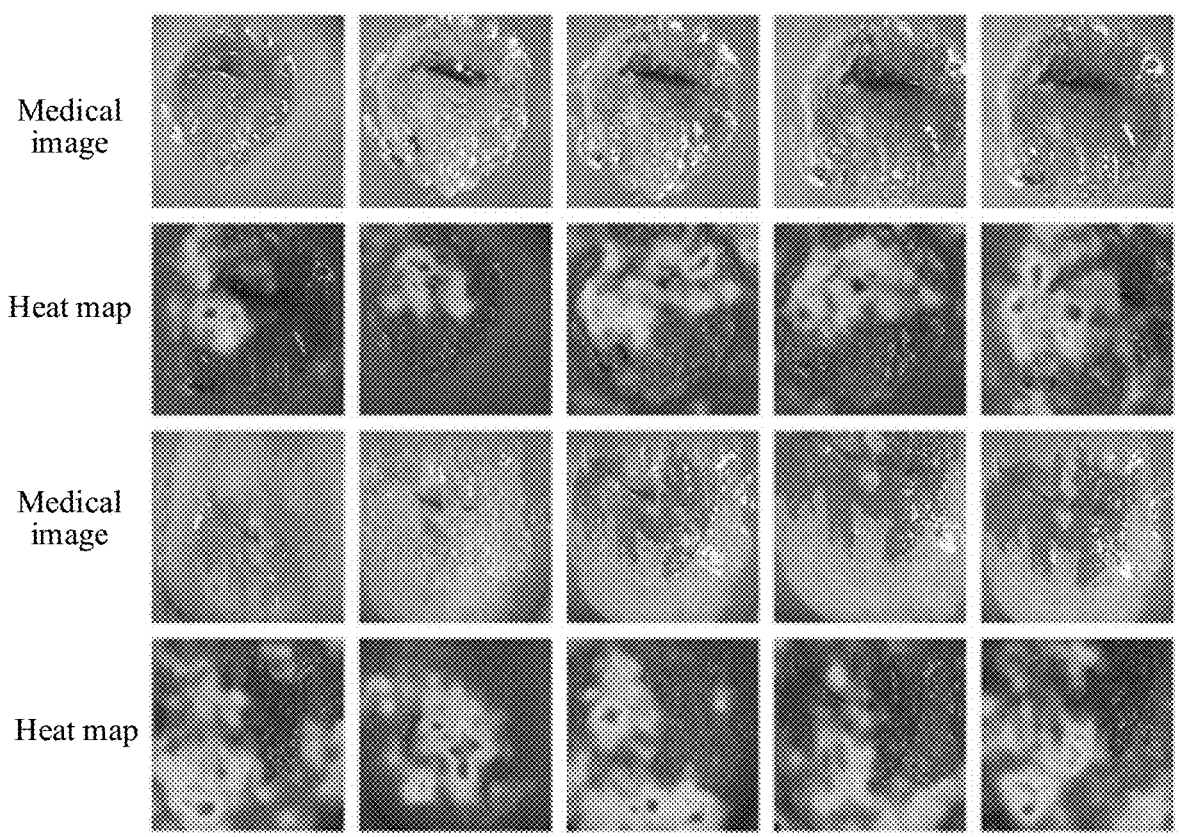
FIG. 12 is a schematic structural diagram of an image recognition model in the related art according to an embodiment of this disclosure.

In addition, referring to medical images and heat maps shown in FIG. 12, the heat maps indicate lesion regions in the corresponding medical images. By comparing the recognition results of this disclosure and the corresponding heat maps, it can be determined that the method provided by the embodiments of this disclosure can accurately recognize the lesion regions in the medical images, with relatively highly accurate recognition results.

The method provided by this embodiment of this disclosure calls the image recognition model to recognize the target object. First, the first extraction network is called to extract the spatial features of the plurality of medical images of the target object; after the spatial feature of each medical image is fully extracted, the second extraction network is called to fuse the plurality of spatial features; and the spatial-temporal feature of the target object is extracted based on the obtained first fusion spatial feature. The spatial-temporal feature can characterize a change in the spatial information of the plurality of medical images at different times. In addition, the temporal relationship between the plurality of medical images is considered during extraction, so that the extracted spatial-temporal feature can more accurately represent the spatial information and the timing information of the plurality of medical images. Therefore, the recognition for the target object based on the spatial-temporal feature by calling the recognition network also improves the accuracy of the recognition result.

In addition, the first extraction network and the second extraction network in this embodiment of this disclosure both use the residual network structure, which alleviates the vanishing gradient problem caused by increasing the depth in the deep neural network. Therefore, more information can be used when extracting the spatial features or extracting the spatial-temporal feature, thereby further improving the accuracy of the spatial features or the spatial-temporal feature.

In addition, in this embodiment of this disclosure, the first extraction network and the second extraction network both use the attention layer. The attention layer can be used to further process the first image feature, so that the processed second image feature can highlight the region feature of the more important image region. Similarly, the attention layer can be used to further process the first fusion spatial feature, so that the processed second fusion spatial features can highlight the spatial feature of the more important medical image.

In this embodiment of this disclosure, the computer device first needs to train the image recognition model before calling the image recognition model for object recognition. The training process includes:

The computer device obtains a plurality of sample images and sample recognition results of the plurality of sample images; calls the image recognition model, to process the plurality of sample images, so as to obtain predicted recognition results of a sample object; and trains the image recognition model according to the sample recognition results and predicted recognition results. The plurality of sample images are images of the same sample object at different times. The computer device performs a plurality of iterative training on the image recognition model, and terminates the iterative training until the number of training times of the image recognition model reaches a reference number, or a training time of the image recognition model is up to a reference time.

In an embodiment, a known colposcopy dataset of timing-lapsed colposcopic images (TCI) is used as a sample dataset of the image recognition model. This sample dataset includes timing-lapsed colposcopic images from 7,668 patients, aged from 24 to 49 years old. These patients are divided into 4 categories, namely non-cancerous (no cancer), cervical intraepithelial neoplasia 1 (CIN1), CIN2-3 and cancer. The CIN1, CIN2-3 and cancer are combined into one category, collectively referred to as low-grade squamous intraepithelial lesions or more severe. 80% of the samples in the sample dataset are used to train the image recognition model, and 20% of the samples are used to test the image recognition model. The sample data of each patient includes images of 5 time nodes (an initial image, an image at 60 seconds, an image at 90 seconds, an image at 120 seconds, and an image at 150 seconds).

In a possible implementation, in the case that the outputted recognition result is a probability, the computer device processes the outputted probability using a cross-entropy loss function or other loss function, and trains the image recognition model according to an outputted result of the loss function.

The computer device that calls the image recognition model for object recognition in FIG. 9 and the computer device that trains the image recognition model may be the same one or different ones. For example, the computer device in this embodiment shown in FIG. 9 is a server or a terminal of a user, and the computer device for training the image recognition model is a terminal or a server of a developer. Alternatively, the computer device in this embodiment shown in FIG. 9 and the computer device for training the image recognition model are the same server.

The image recognition model in this embodiment of this disclosure includes the residual network structure, so a model training process of the image recognition model is simpler, with small calculation amount, thereby significantly improving the training speed of the image recognition model.

Figure 13:
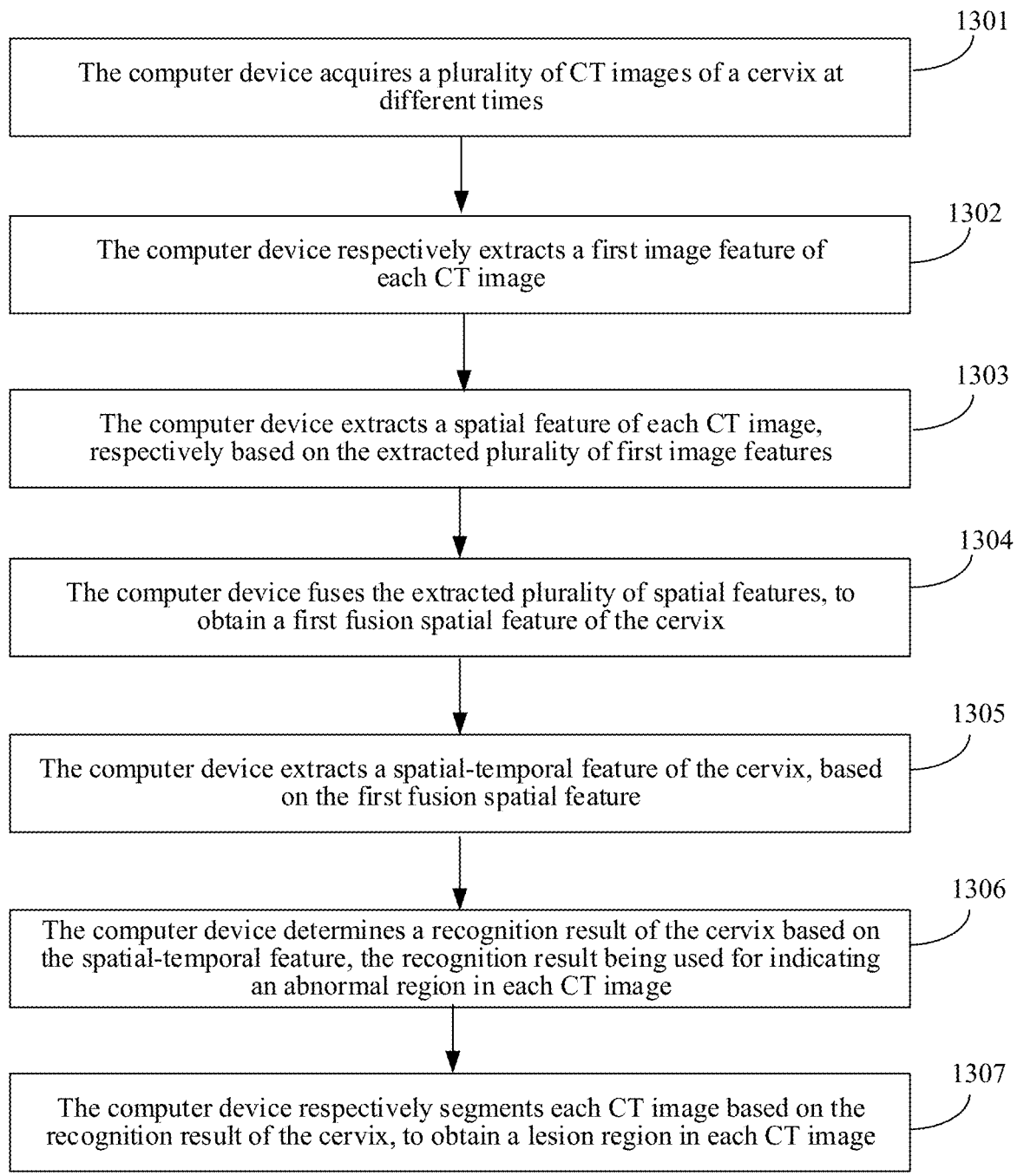
FIG. 13 is a flowchart of an image segmentation method according to an embodiment of this disclosure.

The method provided by the embodiments of this disclosure can be applied to a variety of scenes. In the following description, the image segmentation scene of this disclosure is described with reference to embodiment as shown in FIG. 13.

1301. A computer device acquires a plurality of CT images of a cervix at different times.

1302. The computer device respectively extracts a first image feature of each CT image.

1303. The computer device extracts a spatial feature of each CT image, respectively based on the extracted plurality of first image features.

1304. The computer device fuses the extracted plurality of spatial features, to obtain a first fusion spatial feature of the cervix.

1305. The computer device extracts a spatial-temporal feature of the cervix, based on the first fusion spatial feature.

1306. The computer device determines a recognition result of the cervix based on the spatial-temporal feature. The recognition result is used for indicating an abnormal region in each CT image.

1307. The computer device respectively segments each CT image based on the recognition result of the cervix, to obtain a lesion region in each CT image.

Figure 14:
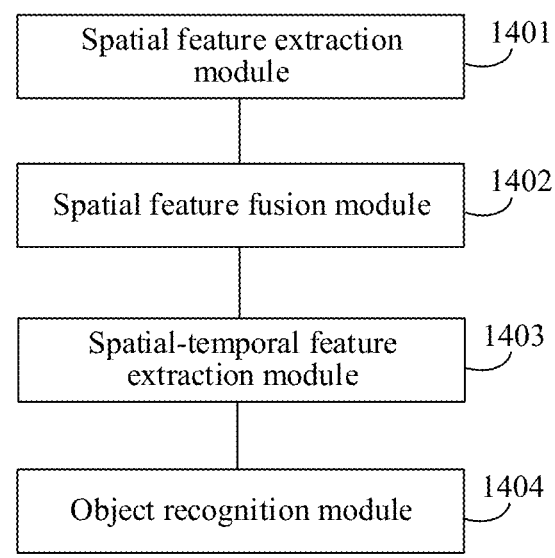
FIG. 14 is a schematic structural diagram of an object recognition apparatus according to an embodiment of this disclosure.

FIG. 14 is a schematic structural diagram of an object recognition apparatus according to an embodiment of this disclosure. Referring to FIG. 14, the apparatus includes:
- a spatial feature extraction module 1401, configured to extract spatial features of a plurality of medical images respectively, the plurality of medical images being images of a same target object at different times;
- a spatial feature fusion module 1402, configured to fuse the extracted plurality of spatial features, to obtain a first fusion spatial feature of the target object;
- a spatial-temporal feature extraction module 1403, configured to extract a spatial-temporal feature of the target object based on the first fusion spatial feature, the spatial-temporal feature characterizing a change in spatial information of the plurality of medical images at different times; and
- an object recognition module 1404, configured to recognize the target object based on the spatial-temporal feature, to obtain a recognition result of the target object.

The apparatus provided by the embodiments of this disclosure first extracts the spatial features of the plurality of medical images of the target object respectively; after the spatial feature of each medical image is fully extracted, fuses the plurality of spatial features; and extracts the spatial-temporal feature of the target object based on the obtained first fusion spatial feature. The spatial-temporal feature can characterize a change in the spatial information of the plurality of medical images at different times. In addition, the temporal relationship between the plurality of medical images is considered during extraction, so that the extracted spatial-temporal feature can more accurately represent the spatial information and the timing information of the plurality of medical images. Therefore, the recognition for the target object based on the spatial-temporal feature improves the accuracy of the recognition result.

Figure 15:
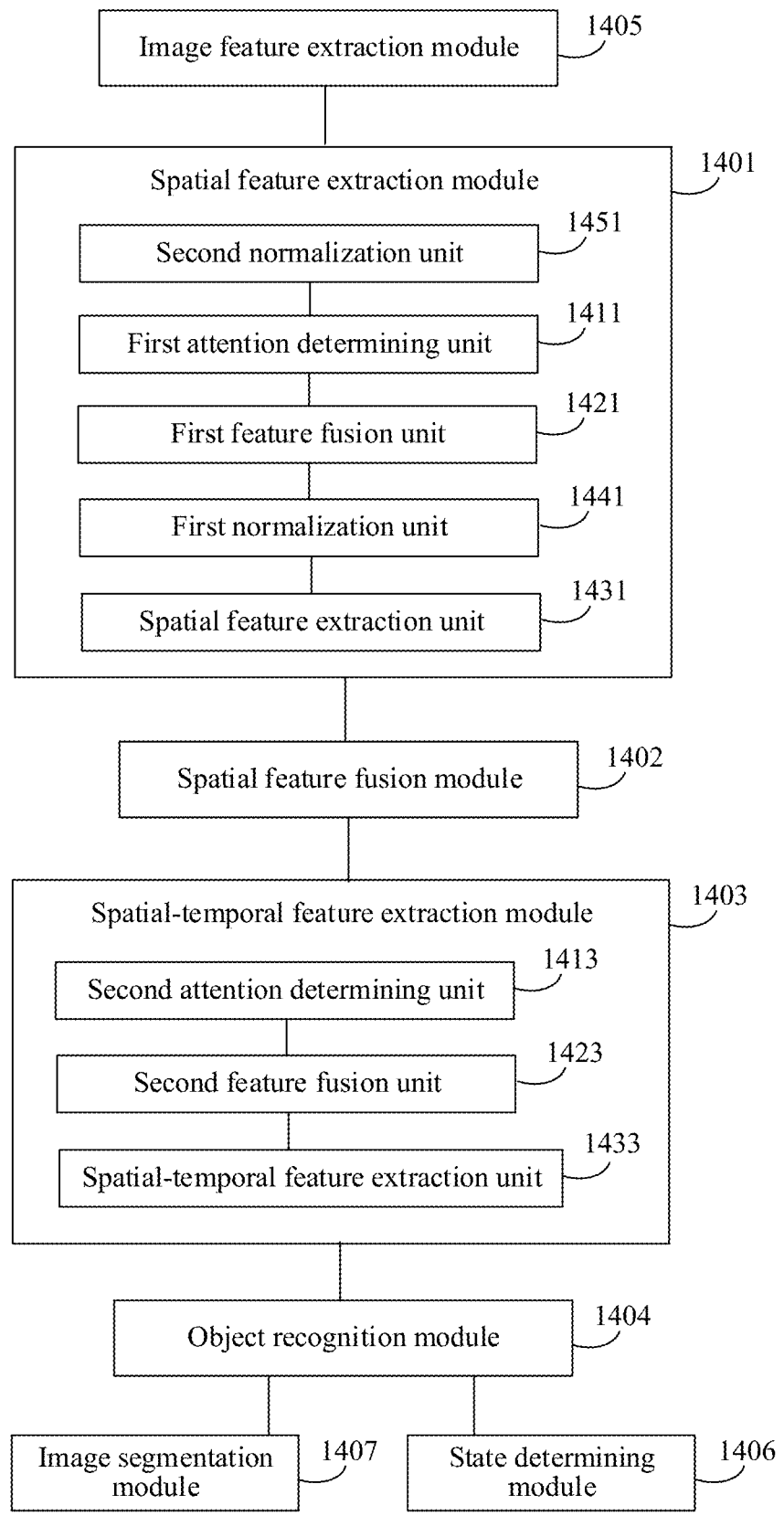
FIG. 15 is a schematic structural diagram of another object recognition apparatus according to an embodiment of this disclosure.

In a possible implementation, referring to FIG. 15, the apparatus further includes:
- an image feature extraction module 1405, configured to extract extracting first image features of the plurality of medical images respectively; and
- the spatial feature extraction module 1401 is configured to extract the spatial features of the plurality of medical images, respectively based on the first image features of the plurality of medical images.

In a possible implementation, referring to FIG. 15, the spatial feature extraction module 1401 includes:
- a first attention determining unit 1411, configured to, for each medical image, segment the first image feature of the medical image into a plurality of region features, and obtain first attention parameters corresponding to the plurality of region features respectively, the first attention parameters characterizing importance degrees of the corresponding region features in the first image feature, the medical image including a plurality of image regions, and each region feature corresponding to one image region in the medical image;
- a first feature fusion unit 1421, configured to perform weighted fusion on the plurality of region features based on a plurality of first attention parameters, to obtain a second image feature corresponding to the medical image; and
- a spatial feature extraction unit 1431, configured to extract the spatial feature of the medical image based on the second image feature.

In a possible implementation, the first attention determining unit 1411 is configured to:
- map each region feature to at least two feature spaces respectively, to obtain at least two mapping features corresponding to each region feature, the at least two feature spaces characterizing a similarity of different pixels in the corresponding image region in a corresponding dimension; and
- obtain the first attention parameter corresponding to each region feature based on the at least two mapping features corresponding to each region feature.

In a possible implementation, the spatial feature extraction unit 1431 is configured to:
- fuse the second image feature and the first image feature, to obtain a third image feature corresponding to the medical image; and
- extract the spatial feature of the medical image based on the third image feature.

In a possible implementation, referring to FIG. 15, the spatial feature extraction module 1401 further includes:
- a first normalization unit 1441, configured to perform normalization processing on the third image feature, to obtain a processed third image feature.

In a possible implementation, referring to FIG. 15, the spatial feature extraction module 1401 further includes:
- a second normalization unit 1451, configured to perform normalization processing on the first image feature of each medical image respectively, to obtain a processed first image feature of each medical image.

In a possible implementation, referring to FIG. 15, the spatial-temporal feature extraction module 1403 includes:
- a second attention determining unit 1413, configured to segment the first fusion spatial feature into a plurality of spatial sub-features, and obtain second attention parameters corresponding to the plurality of spatial sub-features respectively, the second attention parameters characterizing importance degrees of the corresponding spatial sub-features in the first fusion spatial feature, and each spatial sub-feature corresponding to one medical image;
- a second feature fusion unit 1423, configured to fuse the plurality of spatial sub-features based on a plurality of second attention parameters, to obtain a second fusion spatial feature corresponding to the plurality of medical image; and
- a spatial-temporal feature extraction unit 1433, configured to extract the spatial-temporal feature based on the second fusion spatial feature.

In a possible implementation, referring to FIG. 15, the spatial-temporal feature extraction unit 1433 is configured to:

fuse the second fusion spatial feature and the first fusion spatial feature, to obtain a third fusion spatial feature of the target object; and extract the spatial-temporal feature based on the third fusion spatial feature.

In a possible implementation, the recognition result is used for indicating a state of the target object, and referring to FIG. 15, the apparatus further includes:

a state determining module 1406, configured to determine the state of the target object based on the recognition result.

In a possible implementation, the recognition result is used for indicating an abnormal region in each medical image, and referring to FIG. 15, the apparatus further includes:

an image segmentation module 1407, configured to segment each medical image based on the recognition result, to obtain the abnormal region in each medical image.

In a possible implementation, the image recognition model includes a first extraction network, a second extraction network and a recognition network. The spatial feature extraction module 1401 is configured to call the first extraction network, to extract the spatial features of the plurality of medical images respectively;

the spatial feature fusion module 1402 is configured to call the second extraction network, to fuse the extracted plurality of spatial features, so as to obtain the first fusion spatial feature; and the spatial-temporal feature extraction module 1403 is configured to call the second extraction network, to extract the spatial-temporal feature based on the first fusion spatial feature; and the object recognition module 1404 is configured to call the recognition network, to recognize the target object based on the spatial-temporal feature, so as to obtain the recognition result of the target object.

In a possible implementation, the image recognition model further includes a third extraction network, and referring to FIG. 15, the apparatus further includes:

the image feature extraction module 1405, configured to call the third extraction network, to extract first image features of the plurality of medical images respectively; and the spatial feature extraction module 1401, configured to call the first extraction network, to extract the spatial features of the plurality of medical images, respectively based on the first image features of the plurality of medical images.

In a possible implementation, the first extraction network includes a first attention layer and a first extraction layer, and referring to FIG. 14, the spatial feature extraction module 1401 includes:

the first attention determining unit 1411, configured to, for each medical image, call the first attention layer, to segment the first image feature of the medical image into a plurality of region features, and obtain first attention parameters corresponding to the plurality of region features, the first attention parameters characterizing importance degrees of the corresponding region features in the first image feature, each region feature corresponding to one image region in the medical image, and the medical image including a plurality of image regions;

the first feature fusion unit 1421, configured to call the first attention layer, to fuse the plurality of region features according to a plurality of first attention parameters, so as to obtain a second image feature corresponding to the medical image; and the spatial feature extraction unit 1431, configured to call the first extraction layer, to extract the spatial feature of the medical image based on the second image feature.

In a possible implementation, the second extraction network includes a second attention layer and a second extraction layer, and referring to FIG. 14, the spatial-temporal feature extraction module 1403 includes:

the second attention determining unit 1413, configured to call the second attention layer, to segment the first fusion spatial feature into a plurality of spatial sub-features, and obtain second attention parameters corresponding to the plurality of spatial sub-features, the second attention parameters characterizing importance degrees of the corresponding spatial sub-features in the first fusion spatial feature, and each spatial sub-feature corresponding to one medical image;

the second feature fusion unit 1423, configured to call the second attention layer, to fuse the plurality of spatial sub-features based on a plurality of second attention parameters, so as to obtain a second fusion spatial feature corresponding to the plurality of medical images; and the spatial-temporal feature extraction unit 1433, configured to call the second extraction layer, to extract the spatial-temporal feature based on the second fusion spatial feature.

In a possible implementation, a training process of the image recognition model includes:

obtaining a plurality of sample images and sample recognition results to which the plurality of sample images belongs, the plurality of sample images being images of the same sample object at different times;

calling the image recognition model, to process the plurality of sample images, so as to obtain predicted recognition results of a sample object; and training the image recognition model according to the sample recognition results and the predicted recognition results.

All the foregoing technical solutions may be combined in various combinations to form embodiments of this disclosure, and details are not described herein again.

It should be noted that: when the object recognition apparatus provided in the foregoing embodiments identifies an object, the foregoing embodiment is merely described by using an example of dividing various functional modules. In actual application, the foregoing function allocation is completed by different functional modules according to needs, that is, the internal structure of the computer device is divided into different functional modules, to complete all or some of functions described above. In addition, the object recognition apparatus and object recognition method embodiments provided in the foregoing embodiments belong to the same conception. For the specific implementation process, reference may be made to the method embodiments, and details are not described herein again.

The term module (and other similar terms such as unit, submodule, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

An embodiment of this disclosure further provides a computer device. The computer device includes a processor (including processing circuitry) and a memory (including a non-transitory computer-readable storage medium), the memory storing at least one computer program, the at least one computer program being loaded and executed by the processor to implement the operations performed by the object recognition method according to the foregoing embodiment.

Figure 16:
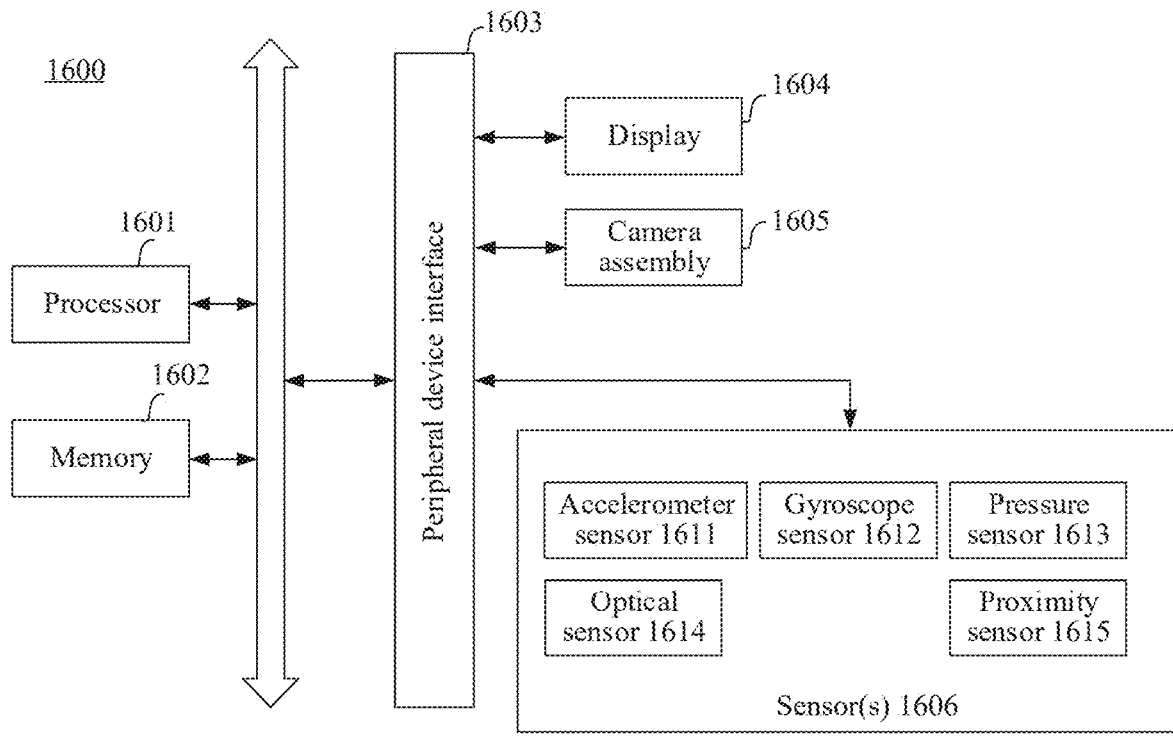
FIG. 16 is a schematic structural diagram of a terminal according to an embodiment of this disclosure.

In an embodiment, the computer device is a terminal. FIG. 16 is a schematic structural diagram of a terminal 1600 according to an embodiment of this disclosure. The terminal 1600 may be a smart phone, a tablet computer, a notebook computer, a desktop computer, a smart speaker, a smart watch, etc. The terminal 1600 may be referred to another name such as a user equipment, a portable terminal, a laptop terminal, or a desktop terminal, etc.

The terminal 1600 include: a processor 1601 and a memory 1602.

The processor 1601 may include one or more processing cores, such as a 4-core processor or an 8-core processor. The processor 1601 may be implemented by at least one hardware form in a digital signal processing (DSP), a field-programmable gate array (FPGA), and a programmable logic array (PLA). In some embodiments, the processor 1601 may further include an artificial intelligence (AI) processor. The AI processor is configured to process a computing operation related to machine learning.

The memory 1602 may include one or more computer-readable storage media that may be non-transitory. In some embodiments, the non-transient computer-readable storage medium in the memory 1602 is configured to store at least one computer program, and the at least one computer program is configured to be executed by the processor 1601 to implement the object recognition method provided in the method embodiments of this disclosure.

In some embodiments, the terminal 1600 may include: a peripheral device interface 1603 and at least one peripheral device. The processor 1601, the memory 1602, and the peripheral device interface 1603 may be connected by using a bus or a signal cable. Each peripheral may be connected to the peripheral interface 1603 by using a bus, a signal cable, or a circuit board. Specifically, the peripheral device includes: at least one of a display screen 1604 and/or a camera assembly 1605.

The peripheral device interface 1603 may be configured to connect at least one input/output (I/O)-related peripheral device to the processor 1601 and the memory 1602. In some embodiments, the processor 1601, the memory 1602, and the peripheral interface 1603 are integrated on the same chip or the same circuit board. In some other embodiments, any one or grouping of two of the processor 1601, the memory 1602, and/or the peripheral device interface 1603 may be implemented on a separate chip or circuit board, which is not limited in this embodiment.

The display screen 1604 is configured to display a user interface (UI). The UI may include a graph, a text, an icon, a video, and any combination thereof. When the display screen 1604 is a touch display screen, the display screen 1604 is further capable of collecting touch signals on or above a surface of the display screen 1604. The touch signal may be inputted, as a control signal, to the processor 1601 for processing.

The camera assembly 1605 is configured to capture an image or a video. In an embodiment, the camera assembly 1605 includes a front-facing camera and a rear-facing camera. The front-facing camera is disposed on the front panel of the terminal, and the rear-facing camera is disposed on a back surface of the terminal.

In some embodiments, the terminal 1600 further includes one or more sensors 1606. The one or more sensors 1606 include but are not limited to: an acceleration sensor 1611, a gyro sensor 1612, a pressure sensor 1613, an optical sensor 1614, and a proximity sensor 1615.

A person skilled in the art may understand that the structure shown in FIG. 16 does not constitute a limitation to the terminal 1600, and the terminal may include more components or fewer components than those shown in the figure, or some components may be combined, or a different component deployment may be used.

Figure 17:
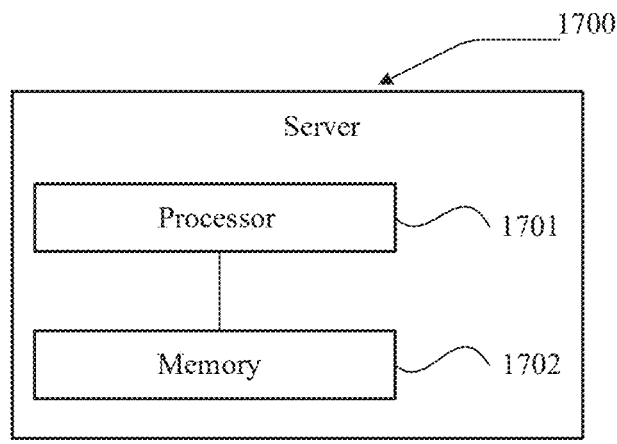
FIG. 17 is a schematic structural diagram of a server according to an embodiment of this disclosure.

In an embodiment, the computer device is provided as a server. FIG. 17 is a schematic structural diagram of a server according to an embodiment of this disclosure. The server 1700 may vary greatly due to different configurations or performance, and may include one or more central processing units (CPUs) 1701 and one or more memories 1702. The memory 1702 stores at least one computer program, the at least one computer program being loaded and executed by the processor 1701 to implement the methods provided in the foregoing method embodiments. Certainly, the server may further include components such as a wired or wireless network interface, a keyboard, and an input/output interface, to facilitate inputs/outputs. The server may further comprise another component configured to implement functions of a device. Details are not described herein again.

An embodiment of this disclosure further provides a computer-readable medium. The computer-readable storage medium storing at least one computer program, the at least one computer program being loaded and executed by the processor to implement the operations performed by the object recognition method according to the foregoing embodiment.

An embodiment of this disclosure further provides a computer program product or a computer program. The computer program product or the computer program stores computer program code, the computer program code being stored in a computer-readable storage medium. A processor of a computer device reads the computer program code from the computer-readable storage medium, and the processor executes the computer program code, to cause the computer device to implement the operations performed in the object recognition method according to the foregoing embodiment.

It should be noted that, In the embodiments of this disclosure, data related to object features, object images, etc. are involved. When the foregoing embodiments of this disclosure are applied to specific products or technologies, the user's permission or consent needs to be obtained, and the acquisition, use and processing of relevant data need to comply with relevant laws, regulations and standards of relevant countries and regions.

A person of ordinary skill in the art may understand that all or some of the steps of the foregoing embodiments may be implemented by hardware, or may be implemented a program instructing related hardware. The program may be stored in a computer-readable storage medium. The storage medium may be: a ROM, a magnetic disk, or an optical disc.

The foregoing disclosure includes some exemplary embodiments of this disclosure which are not intended to limit the scope of this disclosure. Other embodiments shall also fall within the scope of this disclosure.

What is claimed is:

1. An object recognition method, comprising:
extracting first image features of a plurality of medical images respectively by, for each medical image:
segmenting a first image feature of the respective medical image into a plurality of region features, and obtaining first attention parameters respectively corresponding to each of the plurality of region features;
performing weighted fusion on the plurality of region features based on the first attention parameters;
extracting, by a first transformer network, spatial features of the plurality of medical images respectively based on the first image features of the plurality of medical images, the plurality of medical images being images of a same object at different times;
fusing the extracted plurality of spatial features, to obtain a first fusion spatial feature of the object;
extracting, by a second transformer network, a spatial-temporal feature of the object based on the first fusion spatial feature, the spatial-temporal feature indicating a change in the spatial features of the plurality of medical images at the different times; and
recognizing a state of the object based on the spatial-temporal feature, to obtain a recognition result of the object.

2. The method according to claim 1, wherein
the first attention parameters for a respective medical image of the plurality of medical images characterize importance degrees of the corresponding region features in the first image feature of the respective medical image;
the weighted fusion is performed to obtain a second image feature corresponding to the respective medical image; and
the extracting the spatial features includes extracting the spatial feature of the respective medical image based on the second image feature.

3. The method according to claim 2, wherein the obtaining the first attention parameters comprises:
mapping each region feature to at least two feature spaces respectively, to obtain at least two mapping features corresponding to the respective region feature, the at least two feature spaces characterizing a similarity of different pixels in the corresponding image region in a corresponding dimension; and
obtaining the first attention parameter corresponding to the respective region feature based on the at least two mapping features corresponding to the respective region feature.

4. The method according to claim 2, wherein the extracting the spatial feature of the respective medical image based on the second image feature comprises:
fusing the second image feature and the first image feature, to obtain a third image feature corresponding to the respective medical image; and
extracting the spatial feature of the respective medical image based on the third image feature.

5. The method according to claim 4, wherein before the extracting the spatial feature of the respective medical image based on the third image feature, the method further comprises:
performing normalization processing on the third image feature, to obtain a processed third image feature.

6. The method according to claim 2, wherein before the segmenting, the method further comprises:
performing normalization processing on the first image feature of each medical image respectively, to obtain a processed first image feature of each medical image.

7. The method according to claim 1, wherein the extracting the spatial-temporal feature of the object comprises:
segmenting the first fusion spatial feature into a plurality of spatial sub-features, and obtaining second attention parameters corresponding to the plurality of spatial sub-features respectively, the second attention parameters characterizing importance degrees of the corresponding spatial sub-features in the first fusion spatial feature, and each spatial sub-feature corresponding to one medical image;
fusing the plurality of spatial sub-features based on a plurality of second attention parameters, to obtain a second fusion spatial feature corresponding to the plurality of medical images; and
extracting the spatial-temporal feature based on the second fusion spatial feature.

8. The method according to claim 7, wherein the extracting the spatial-temporal feature based on the second fusion spatial feature comprises:
fusing the second fusion spatial feature and the first fusion spatial feature, to obtain a third fusion spatial feature of the object; and
extracting the spatial-temporal feature based on the third fusion spatial feature.

9. The method according to claim 1, wherein
the method is performed based on an image recognition model, the image recognition model comprises the first transformer network, the second transformer network and a recognition network, and
the extracting the spatial features of the plurality of medical images respectively comprises:
calling the first transformer network, to extract the spatial features of the plurality of medical images respectively;
the fusing the extracted plurality of spatial features comprises:
calling the second transformer network, to fuse the extracted plurality of spatial features, so as to obtain the first fusion spatial feature;
the extracting the spatial-temporal feature of the object based on the first fusion spatial feature comprises:
calling the second transformer network, to extract the spatial-temporal feature based on the first fusion spatial feature; and
the recognizing the state of the object based on the spatial-temporal feature comprises:
calling the recognition network, to recognize the state of the object based on the spatial-temporal feature, so as to obtain the recognition result of the object.

10. The method according to claim 9, wherein
the image recognition model further comprises an extraction network, and
the method further comprises:
before the calling the first transformer network to extract the spatial features of the plurality of medical images,
calling the third Transformer extraction network, to extract first image features of the plurality of medical images respectively; and
the calling the first transformer network, to extract the spatial features of the plurality of medical images respectively comprises:
calling the first transformer network, to extract the spatial features of the plurality of medical images, respectively based on the first image features of the plurality of medical images.

11. The method according to claim 10, wherein
the first transformer network comprises a first attention layer and a first extraction layer, and
the calling the first transformer network, to extract the spatial features of the plurality of medical images respectively comprises:
for each medical image,
calling the first attention layer, to segment a first image feature of the respective medical image into a plurality of region features, and obtain first attention parameters respectively corresponding to each of the plurality of region features, the first attention parameters characterizing importance degrees of the corresponding region features in the first image feature, each region feature corresponding to one image region in the respective medical image, and the respective medical image comprising a plurality of image regions;
calling the first attention layer, to fuse the plurality of region features according to the first attention parameters, so as to obtain a second image feature corresponding to the respective medical image; and
calling the first extraction layer, to extract a spatial feature of the respective medical image based on the second image feature.

12. An object recognition apparatus, comprising:
processing circuitry configured to:
extract first image features of a plurality of medical images respectively by, for each medical image:
segmenting a first image feature of the respective medical image into a plurality of region features, and obtaining first attention parameters respectively corresponding to each of the plurality of region features;
performing weighted fusion on the plurality of region features based on the first attention parameters;
extract, by a first transformer network, spatial features of the plurality of medical images respectively based on the first image features of the plurality of medical images, the plurality of medical images being images of a same object at different times;
fuse the extracted plurality of spatial features, to obtain a first fusion spatial feature of the object;
extract, by a second transformer network, a spatial-temporal feature of the object based on the first fusion spatial feature, the spatial-temporal feature indicating a change in the spatial features of the plurality of medical images at the different times; and
recognize a state of the object based on the spatial-temporal feature, to obtain a recognition result of the object.

13. The apparatus according to claim 12, wherein
the first attention parameters for a respective medical image of the plurality of medical images characterize importance degrees of the corresponding region features in the first image feature of the respective medical image;
the weighted fusion is performed to obtain a second image feature corresponding to the respective medical image; and
the processing circuitry is configured to extract the spatial feature of the respective medical image based on the second image feature.

14. The apparatus according to claim 13, wherein the processing circuitry is further configured to:
map each region feature to at least two feature spaces respectively, to obtain at least two mapping features corresponding to the respective region feature, the at least two feature spaces characterizing a similarity of different pixels in the corresponding image region in a corresponding dimension; and
obtain the first attention parameter corresponding to the respective region feature based on the at least two mapping features corresponding to the respective region feature.

15. The apparatus according to claim 13, wherein the processing circuitry is further configured to:
fuse the second image feature and the first image feature, to obtain a third image feature corresponding to the respective medical image; and
extract the spatial feature of the respective medical image based on the third image feature.

16. The apparatus according to claim 15, wherein the processing circuitry is further configured to:
before extracting the spatial feature of the respective medical image based on the third image feature, perform normalization processing on the third image feature, to obtain a processed third image feature.

17. The apparatus according to claim 13, wherein the processing circuitry is further configured to:
before segmenting the first image feature of each respective medical image into the plurality of region features, perform normalization processing on the first image feature of each medical image respectively, to obtain a processed first image feature of each medical image.

18. A non-transitory computer-readable storage medium storing computer-readable instructions thereon, which, when executed by processing circuitry, cause the processing circuitry to perform an object recognition method comprising:
extracting first image features of a plurality of medical images respectively by, for each medical image:
segmenting a first image feature of the respective medical image into a plurality of region features, and obtaining first attention parameters respectively corresponding to each of the plurality of region features;
performing weighted fusion on the plurality of region features based on the first attention parameters;
extracting, by a first transformer network, spatial features of the plurality of medical images respectively based on the first image features of the plurality of medical images, the plurality of medical images being images of a same object at different times;
fusing the extracted plurality of spatial features, to obtain a first fusion spatial feature of the object;
extracting, by a second transformer network, a spatial-temporal feature of the object based on the first fusion spatial feature, the spatial-temporal feature indicating a change in the spatial features of the plurality of medical images at the different times; and
recognizing a state of the object based on the spatial-temporal feature, to obtain a recognition result of the object.

* * * * *